United States Patent [19]
Jilka et al.

[11] Patent Number: 5,986,175
[45] Date of Patent: Nov. 16, 1999

[54] VIRUS RESISTANT PLANTS

[75] Inventors: Joseph Maria Jilka, Ankeny, Iowa; Nilgun Ereken Tumer, Chesterfield, Mo.

[73] Assignee: Monsanto Company, St. Louis, Mich.

[21] Appl. No.: 08/559,221

[22] Filed: Nov. 16, 1995

Related U.S. Application Data

[63] Continuation of application No. 08/368,260, Jan. 3, 1995, Pat. No. 5,503,999, which is a continuation of application No. 08/147,416, Nov. 5, 1993, abandoned, which is a continuation of application No. 07/910,224, Jul. 9, 1992, abandoned.

[51] Int. Cl.$^6$ .............................. A01H 5/00; C12N 15/82; C12N 15/33
[52] U.S. Cl. ........................ 800/301; 800/280; 435/418; 435/419; 536/23.72
[58] Field of Search ........................... 800/205, DIG. 40, 800/42, 43, 44, 298, 301, 280, 317, 317.1, 317.2, 317.3, 307, 320.1, 320.3, 313

[56] References Cited

U.S. PATENT DOCUMENTS

| | | | |
|---|---|---|---|
| 5,580,716 | 12/1996 | Johnston et al. | |
| 5,596,132 | 1/1997 | Zaitlin et al. | 800/205 |
| 5,633,449 | 5/1997 | Zaitlin et al. | 800/205 |

FOREIGN PATENT DOCUMENTS 636717  3/1992  Australia .

OTHER PUBLICATIONS

Audy et al., (1992) "Transformation of Potato and Tobacco with Modified Replicase Genes of Potato Viruses Y and Leafroll," Canadian Journal of Plant Pathology, 14 240–249 (meeting abstract).
Audy et al. (1994) Mol. Plant–Microbe Int. 7(1): 15–21.
Kaniewski et al., (1990) Bio Technology 8: 750–753.
Golemoski et al., (1990) Proc. Natl. Acad. Sci. 87: 6311–6315.
Sanger et al., (1990) Plant Mol. Biol. 14: 433–443.
Mori et al., (1992) J. Gen. Virology 73: 169–172.
Hanley–Bowdoin et al., (1990) Proc. Natl. Acad. Sci. 87: 1446–1450.
Carr et al. (1992) *Molecular Plant Microbe Interactions* 5(5);397–404. Resistance to tobacco mosaic virus induced by the 54–kDa gene sequence requires expression of the 54–kDa protein.
Donson et al. (1993) *Molecular Plant Microbe Interactions* 6(5):635–642. Broad resistance to tobamoviruses is mediated by a modified tobacco mosaic virus replicase transgene.
McFarlane and Davies (1992) *Proc. Natl. Acad. Sci. USA* 89:5829–5833. Plants transformed with a region of the 201–kilodalton replicase gene from pea early browning virus RNA1 are resistant to virus infection.
Taschner et al. (1991) *Virology* 181:445–450. Replication of an incomplete alfalfa mosaic virus genome in plants transformed with viral replicase genes.
Longstaff et al. (1993) *EMBO J.* 12(2):379–386. Extreme resistance to potato virus X infection in plants expressing a modified component of the putative viral replicase.
Anderson et al. (1992) *Proc. Natl. Acad. Sci. USA* 89:8759–8763. A defective replicase gene induces resistance to cucumber mosaic virus in transgenic tobacco plants.
Day et al. (1991) *Proc. Natl. Acad. Sci. USA* 88: 6721–6725. Expression of an antisense viral gene in transgenic tobacco confers resistance to the DNA virus tomato golden mosaic virus.
Braun and Hemenway (1992) *The Plant Cell* 4:735–744. Expression of amino–terminal portions or full–length viral replicase genes in transgenic plants confers resistance to potato virus X infection.
Audy et al (1994) Molec. Plant–Microbe Intractions 7 (1): 15–22.

*Primary Examiner*—Elizabeth F. McElwain
*Attorney, Agent, or Firm*—Grace L. Bonner; Arnold White & Durkee

[57] ABSTRACT

An isolated DNA sequence which codes for a potyvirus replicase gene is disclosed herein. A method for providing resistance to infection by a virus by expressing a replicase gene in plants is also disclosed. Transgenic potato plants and tubers containing the replicase gene are also disclosed.

13 Claims, 8 Drawing Sheets

FIG. 1A

```
    ATGGCTAAGCATTCTGCATGGATGTTTGAAGCCTTGACGGGAAAATTTGCAAGCTGTCGCA
1   ------+---------+---------+---------+---------+---------+   60
    TACCGATTCGTAAGACGTACCTACAAACTTCGGAACTGCCCTTTTAAACGTTCGACAGCGT

M  A  K  H  S  A  W  M  F  E  A  L  T  G  N  L  Q  A  V  A

ACAATGAAGAGCCAATTAGTAACCAAGCATGTAGTTAAAGGAGAGTGTCGACACTTCAAG
61  ------+---------+---------+---------+---------+---------+  120
    TGTTACTTCTCGGTTAATCATTGGTTCGTACATCAATTTCCTCTCACAGCTGTGAAGTTC

T  M  K  S  Q  L  V  T  K  H  V  V  K  G  E  C  R  H  F  K

GAATTCCTGACTGTGGATGCAGAGGCAGAGGCAGAGGCCATTCTTCAGGCCTTTGATGGAT
121 ------+---------+---------+---------+---------+---------+  180
    CTTAAGGACTGACACCTACGTCTCCGTCTCCGTCTCCGGTAAGAAGTCCGGAAACTACCTA

E  F  L  T  V  D  A  E  A  E  A  E  A  F  F  R  P  L  M  D

GCGTATGGGAAAAGCTTGCTGAACAGAGATGCGTACATCAAGGACATAATGAAGTATTCA
181 ------+---------+---------+---------+---------+---------+  240
    CGCATACCCTTTTCGAACGACTTGTCTCTACGCATGTAGTTCCTGTATTACTTCATAAGT

A  Y  G  K  S  L  L  N  R  D  A  Y  I  K  D  I  M  K  Y  S
```

```
241 AAACCTATAGATGTTGGTATCGTGGATCGGATGCATTCGAGGAAGCCATCAATAGGGTTA 300
    ---------+---------+---------+---------+---------+---------+
    TTTGGATATCTACAACCATAGCACCTAGCCTACGTAAGCTCCTTCGGTAGTTATCCCAAT
     K  P  I  D  V  G  I  V  D  R  M  H  S  R  K  P  S  I  G  L

301 TCATCTACCTGCAATGTGCACGGCTTCAAGAAGTGTGCATATGTCACTGACGAGCAAGAA 360
    ---------+---------+---------+---------+---------+---------+
    AGTAGATGGACGTTACACGTGCCGAAGTTCTTCACACGTATACAGTGACTGCTCGTTCTT
     S  S  T  C  N  V  H  G  F  K  K  C  A  Y  V  T  D  E  Q  E

361 ATTTTCAAAGGCGCTCAACATGAAAGCTGCAGTCGGAGCCAGTTATGGGTGCAAAAAGAAA 420
    ---------+---------+---------+---------+---------+---------+
    TAAAAGTTTCGCGAGTTGTACTTTCGACGTCAGCCTCGGTCAATACCCACGTTTTTCTTT
     I  F  K  A  L  N  M  K  A  A  V  G  A  S  Y  G  C  K  K  K

421 GACTATTTTGAGCATTTCACTGATGCAGATAAGGAAGAAATAGTCATGCAAAGCTGTCTG 480
    ---------+---------+---------+---------+---------+---------+
    CTGATAAAACTCGTAAAGTGACTACGTCTATTCCTTCTTTATCAGTACGTTTCGACAGAC
     D  Y  F  E  H  F  T  D  A  D  K  E  E  I  V  M  Q  S  C  L
```

```
     CGATTGTATAAAGGCTTGCTCGGCATTTGGAATGGATCATTGAAGGCAGAGCTCCAATGT
481  ------------+---------+---------+---------+---------+---------+ 540
     GCTAACATATTTCCGAACGAGCCGTAAACCTTACCTAGTAACTTCCGTCTCGAGGTTACA

R   L   Y   K   G   L   L   G   I   W   N   G   S   L   K   A   E   L   Q   C

AAGGAAAAGATACTTGCAAATAAGACGAGGACGTTCACTGCTGCACCTCTAGACACTTTG
541  ------------+---------+---------+---------+---------+---------+ 600
     TTCCTTTTCTATGAACGTTTATTCTGCTCCTGCAAGTGACGACGTGGAGATCTGTGAAAC

K   E   K   I   L   A   N   K   T   R   T   F   T   A   A   P   L   D   T   L

CTGGGTGGTAAAGTGTGTGTTGACGACTTCAATAATCAATTTTATTGAAGAATATTGAG
601  ------------+---------+---------+---------+---------+---------+ 660
     GACCCACCATTTCACACACAACTGCTGAAGTTATTAGTTAAAATAAGCTTCTTATAACTC

L   G   G   M   V   C   V   D   D   F   N   N   Q   F   Y   S   K   N   I   E

TGCTGTGGACAGTTGGGATGACTAAGTTTTATGGCGGTTGGGATAAACTGCTTCGGCGT
661  ------------+---------+---------+---------+---------+---------+ 720
     ACGACAACCTGTCAACCCTACTGATTCAAAATACCGCCAACCCTATTTGACGAAGCCGCA

```
     TTACCTGAGAATTGGGTATACTGTGATGCTGAGGGCTCACAGTTTGATAGTTCACTAACT
721  ------------+---------+---------+---------+---------+---------+  780
     AATGGACTCTTAACCCATATGACACTACGACTGCCGAGTGTCAAACTATCAAGTGATTGA

L  P  E  N  W  V  Y  C  D  A  D  G  S  Q  F  D  S  S  L  T

CCATACTTAATCAATGCTGTTCTCACCATCAGAAGCACGTACATGGAAGACTGGGATGTG
781  ------------+---------+---------+---------+---------+---------+  840
     GGTATGAATTAGTTACGACAAGAGTGGTAGTCTTCGTGCATGTACCTTCTGACCCTACAC

P  Y  L  I  N  A  V  L  T  I  R  S  T  Y  M  E  D  W  D  V

GGGTTGCAAATGCTGAGTAATTTATACACTGAGATTGTTTACACACCTATTTCAACTCCA
841  ------------+---------+---------+---------+---------+---------+  900
     CCCAACGTTTACGACTCATTAAATATGTGACTCTAACAAATGTGTGGATAAAGTTGAGGT

G  L  Q  M  L  S  N  L  Y  T  E  I  V  Y  T  P  I  S  T  P

GATGGAACAATTGTTAAGAAGTTCAGAGGAAATAACAGTGGTCAGCCTTCTACTGTTGTG
901  ------------+---------+---------+---------+---------+---------+  960
     CTACCTTGTTAACAATTCTTCAAGTCTCCTTTATTGTCACCAGTCGGAAGATGACAACAC

```
961  GACAACTCTCTTATGGTGTCGTCCTTGCCATGCACTATGCTTTCATCAAAGAATGCATTGAG  1020
     ---------+---------+---------+---------+---------+---------+
     CTGTTGAGAGAATACCACAGCAGGAACGGTACGTGATACGAAAGTAGTTTCTTACGTAACTC

D  N  S  L  M  V  V  L  A  M  H  Y  A  F  I  K  E  C  I  E  -

1021 TTTGAAGAGATTGACAGCACGTGCGTGTTCTTTGTCAATGGTGATGATTTGCTGATTGCT   1080
     ---------+---------+---------+---------+---------+---------+
     AAACTTCTCTAACTGTCGTGCACGCACAAGAAACAGTTACCACTACTAAACGACTAACGA

F  E  E  I  D  S  T  C  V  F  F  V  N  G  D  D  L  L  I  A  -

1081 GTGAATCCGGATAAAGAGAGCATTCTTGACAGATTGTCACACACTTCTCAGATCTTGGT   1140
     ---------+---------+---------+---------+---------+---------+
     CACTTAGGCCTATTTCTCTCGTAAGAACTGTCTAACAGTGTTGTGAAGAGTCTAGAACCA

V  N  P  D  K  E  S  I  L  D  R  L  S  Q  H  F  S  D  L  G  -

1141 TTGAATTATGATTTTTCGTCAAAGACAAGAAATAAGGAAGAGTTGTGGTTTATGTCTCAT   1200
     ---------+---------+---------+---------+---------+---------+
     AACTTAATACTAAAAGCAGTTTCTGTTCTTTATTCCTTCTCAACACCAAATACAGAGTA

```
     AGGGGCCTACTGATTGAGGGCATGTACGTGCCGAAACTTGAAGAGGAAGGATTTGTGTCC
1201 ------+---------+---------+---------+---------+---------+ 1260
     TCCCCGGATGACTAACTCCCGTACATGCACGGCTTTGAACTTCTCCTTCCTAAACACAGG

R  G  L  L  I  E  G  M  Y  V  P  K  L  E  E  E  G  F  V  S

ATTCTCCAATGGGACAGAGCAGACTTGGCTGAACACAGGCTTGAGGCGATTTGCGCAGCT
1261 ------+---------+---------+---------+---------+---------+ 1320
     TAAGAGGTTACCCTGTCTCGTCTGAACCGACTTGTGTCCGAACTCCGCTAAACGCGTCGA

I  L  Q  W  D  R  A  D  L  A  E  H  R  L  E  A  I  C  A  A

ATGATAGAGTCCTGGGGTTATTCTGAACTAACACACCAAATCAGGAGATTCTACTCATGG
1321 ------+---------+---------+---------+---------+---------+ 1380
     TACTATCTCAGGACCCCAATAAGACTTGATTGTGTGGTTTAGTCCTCTAAGATGAGTACC

M  I  E  S  W  G  Y  S  E  L  T  H  Q  I  R  R  F  Y  S  W

TTATTGCAACAGCAACCTTTTGCAACAATAGGCGCAGGAAGGGAAGGCTCCTTATATAGCA
1381 ------+---------+---------+---------+---------+---------+ 1440
     AATAACGTTGTCGTTGGAAAACGTTGTTATCGCGTCCTTCCCTTCCGAGGAATATATCGT

L  L  Q  Q  Q  P  F  A  T  I  A  Q  E  G  K  A  P  Y  I  A
```

```
                AGCATGGCACTAAGGAAACTGTATATGGATAGGGCTGTGGATGAGGAAGAGCTAAGAGCC
1441    --------+---------+---------+---------+---------+---------+   1500
                TCGTACCGTGATTCCTTTGACATATACCTATCCCGACACCTACTCCTTCTGATTCTCGG

S  M  A  L  R  K  L  Y  M  D  R  A  V  D  E  E  E  L  R  A

TTCACTGAAATGATGGTCGCATTAGACGATGAGTTTGAGTTTGACTCTTATGAAGTACAC
1501    --------+---------+---------+---------+---------+---------+   1560
                AAGTGACTTTACTACCAGCGTAATCTGCTACTCAAACTCAAACTGAGAATACTTCATGTG

F  T  E  M  M  V  A  L  D  D  E  F  E  F  D  S  Y  E  V  H

CATCAATAGAATGGATCTCTAGAGTCGACCTGCAGGCATGCAAGCTTCAGCTGCTCGAG
1561    --------+---------+---------+---------+---------+---------+   1620
                GTAGTTATCTTACCTAGGAGATCTCAGCTGGACGTCCGTACGTTCGAAGTCGACGAGCTC

H  Q  *  N  G  S  S  R  V  D  L  Q  A  C  K  L  Q  L  L  E

TTCTATAGTGTCGCCTAAATCGTATGTGTATGATACATAAGGGTTATGTATTAATTGTAG
1621    --------+---------+---------+---------+---------+---------+   1680
                AAGATATCACAGCGGATTTAGCATACACATACTATGTATTCCCAATACATAATTAACATC

F  Y  S  V  A  *  I  V  C  V  *  Y  I  R  V  M  Y  *  L  *

CCGCGTTCTAACGACAATATGTCCATATGGTGACCTCAGTACAACTGCTCTGATGCCGC
1681    --------+---------+---------+---------+---------+---------+   1739
                GGCGCAAGATTGCTGTTATACAGGTATACCACTGGAGTCATGTTGACGAGACTACGGCG
```

FIG. 1G

VIRUS RESISTANT PLANTS

This application is a continuation of U.S. Ser. No. 08/368,260 filed Jan. 3, 1995, now U.S. Pat. No. 5,503,999, which is a Continuation of U.S. Ser. No. 08/147,416 filed Nov. 5, 1993, now abandoned, which is a Continuation of U.S. Ser. No. 07/910,224 filed Jul. 9, 1992, now abandoned.

FIELD OF THE INVENTION

This invention is related to the genetic engineering of plants and to a means and method for conferring viral resistance to a plant using a gene encoding a potyvirus replicase.

BACKGROUND OF THE INVENTION

Many agriculturally important crops are susceptible to infection by plant viruses. These viruses can seriously damage a crop and drastically reduce its economic value to the grower. This eventually leads to a higher cost for the consumer. Attempts to control or prevent infection of a crop by a plant virus have been made, yet viral pathogens continue to be a significant problem in agriculture.

Scientists have recently developed means to produce virus resistant plants using genetic engineering techniques. Such an approach is advantageous in that the means for providing the protection is incorporated in the plant itself and can be passed on to its progeny. A host plant is resistant if it possesses the ability to suppress or retard the multiplication of a virus, or the development of pathogenic symptoms. "Resistant" is the opposite of "susceptible", and may be divided into: (1) high, (2) moderate, or (3) low resistance, depending upon its effectiveness. Essentially, a resistant plant shows reduced or no symptom expression, and virus multiplication within it is reduced or negligible. Several different types of host resistance to viruses are recognized. The host may be resistant to: (1) establishment of infection, (2) virus multiplication, or (3) viral movement.

It has previously been shown that expression of a plant virus capsid protein, which is termed the coat protein, in a plant can confer resistance to the homologous virus and to related viruses (Abel et al. 1986; Turner et al. 1987: Cuozzo et al. 1988; Hemenway et al. 1988; Stark and Beachy 1989; Lawson et al. 1990; Kaniewski et al. 1990). In these studies, resistance to virus disease is defined as either reduced incidence of infection, delayed symptom development, reduced virus replication or viral antigen levels, or slower to no systemic virus movement. Expression of the virus coat protein in these transgenic plants is responsible for the observed effects in the reduction of virus disease by an as yet undetermined mechanism (Abel et al. 1986; van Dun et al. 1988). This type of protection against viral infection is termed coat protein-mediated protection.

Even though coat protein-mediated viral resistance has proven to be useful in variety of situations, it may not always be the most effective or the most desirable means for providing viral resistance. In such instances, it would be advantageous to have other methods for conferring viral resistance to plants.

A fragment of the putative replicase gene from tobacco mosaic virus (TMV) recently has been found to provide resistance against TMV when expressed in tobacco plants (Golemboski et al. 1990). In TMV, two proteins, the 183 kDa and 126 kDa proteins, have been speculated to be replicase components, as the expression of both proteins are necessary for normal multiplication in tobacco plants (Ishikawa et al. 1986). The 183 kDa protein is a read-through product of the 126 kDa sequence. The 126 kDa protein contains the NTP binding motif. The 183 kDa protein contains both the NTP and GDD motifs. More specifically, the 54 kDa readthrough portion of the 183 kDa protein is the portion that contains the GDD motif. Golemboski et al. (1990) found that transgenic tobacco plants expressing the 54 kDa read-through portion were protected against infection by TMV. They did not, however, observe protection in transgenic plants expressing the larger 126 kDa protein. Moreover, they did not report any protection data from experiments in which the plants expressed the 183 kDa protein.

Others have conducted protection experiments with transgenic plants expressing components of non-structural viral proteins. For example, van Dun et al. (1988) analyzed protection in tobacco plants expressing either of two genes encoding proteins involved in the replication of alfalfa mosaic virus (AlMV). These plants were transformed with RNAs 1 or 2 of AlMV, which encode proteins P1 and P2, respectively. The polypeptides encoded by these RNAs have amino acid homologies to other viral replicases, and both RNAs are known to be essential for replication. The PVY ORF1, the NTP and GDD binding motifs for AlMV reside on different RNAs and consequently different proteins. The replicase protein here also contains the GDD domain found in many proteins capable of replicating nucleic acids (Hodgman, 1981). The GDD domain contains a glycine amino acid residue (G) followed by two aspartate amino acid residues (D). GDD domains are often found in replicase proteins and are believed to be involved in catalytic function. In particular, P1 on RNA1 has homology to the NTP binding motif and P2 on RNA2 has homology to the GDD motif. Plants expressing either RNA1 or RNA2 were not protected against infection by AlMV. In addition, plants expressing both RNAs 1 and 2 were likewise not protected against infection by AlMV (Taschner et al. 1991).

Buck et al. (PCT publication WO 92/03539) have described the use of various techniques to prevent the expression or function of a cucumber mosaic viral replicase in order to provide viral resistance in plants, including the expression of a fragment of the replicase gene in order to provide this viral resistance. The techniques employed or disclosed in this publication to accomplish this included: (1) antisense technology (wherein a complementary RNA to that coding for the full length replicase was expressed); (2) expression of a gene coding for an antibody specific for one of the three components of the replicase (viral encoded polypeptides P1a and P2a, and polypeptide P50 from tobacco); (3) a truncated form or fragment of the replicase; and (4) use of a ribozyme specific for the RNA coding for one of the components of the replicase.

Potato virus Y (hereinafter PVY) is a member of the potyvirus plant virus group. The potyvirus group of plant viruses comprises the largest group of plant viruses which flourish in a wide range of crops and environmental conditions. Representative members of the potyvirus group include, but are not limited to, potato virus Y (PVY), tobacco vein mottling virus, watermelon mosaic virus, zucchini yellow mosaic virus, bean common mosaic virus, bean yellow mosaic virus, soybean mosaic virus, peanut mottle virus, beet mosaic virus, wheat streak mosaic virus, maize dwarf mosaic virus, sorghum mosaic virus, sugarcane mosaic virus, johnsongrass mosaic virus, plum pox virus, tobacco etch virus, sweet potato feathery mottle virus, yam mosaic virus, and papaya ringspot virus. PVY is a positive-sense, single-stranded RNA virus that is surrounded by a repeating proteinaceous monomer, which is termed the coat protein (CP). The encapsidated virus has a flexous rod morphology, which is characteristic of the potyvirus group. The majority of the potyviruses are transmitted in a non-persistent manner by aphids. A list of potyviruses causing serious annual crop losses and the crop species affected are shown in Table 1. As can be seen from the wide range of crops affected by potyviruses, the host range includes such diverse families of plants, but is not limited to Solanaceae, Chenopodiaceae, Gramineae, Compositae, Leguminosae, Dioscoreaceae, Cucurbitaceae, and Caricaceae. The various potyviruses also demonstrate cross-infectivity between plant members of the different families.

TABLE 1

Representative Potyviruses causing serious annual crop losses and the crop species affected

| | |
|---|---|
| Potato virus Y | potato, tobacco, tomato, pepper |
| Tobacco etch | tomato, pepper |
| Watermelon mosaic | cucurbits |
| Zucchini yellow mosaic | cucurbits |
| Bean common mosaic | Phaseolus sp. |
| Bean yellow mosaic | Phaseolus sp. |
| Soybean mosaic | soybeans |
| Peanut mottle | peanuts, beans, soybeans, peas |
| Beet mosaic | sugarbeets, spinach |
| Wheat streak mosaic | small grains, e.g. wheat |
| Maize dwarf mosaic | corn, sugarcane, sorghum |
| Sorghum mosaic | corn, sugarcane, sorghum |
| Johnsongrass mosaic | corn, sugarcane, sorghum |
| Plum pox | plum, peach, nectarine, apricot |
| Papaya ringspot | papaya |
| Tobacco vein mottling | tobacco |
| Sugar cane mosaic | sugarcane |
| yam mosaic | yam |
| sweet potato feathery mottle | sweet potato |

The host range of PVY is mainly restricted to members of the Solanaceae family, including potato, tobacco, and tomato (Purcifull and Edwardson, 1981). Potato plants are particularly susceptible to infection by PVY. Infection by PVY of a potato crop results in a substantially reduced yield. Moreover, simultaneous infection by PVY and the potexvirus Potato virus X (PVX) causes a devastating synergistic effect. A combined PVY and PVX infection can reduce yields as much as 90% (deBokx, 1986; Vance 1991). Other synergistic infectious relationships between a potyvirus and another type of plant virus are also known to exist. Further examples of this synergism include the following: (1) the combined infection of maize dwarf mosaic virus (a potyvirus) and maize chlorotic mottle virus in corn to produce a disease known as corn lethal necrosis; and (2) the combined infection of potato virus Y (a potyvirus) and cucumber mosaic virus in tomato. This synergistic relationship between the viruses during the course of infection is in all cases marked by a dramatic increase in the total damage generated in the plant.

PVY is an aphid-transmitted virus. Because of the ease of transmission of the virus by aphids, potato growers must adhere to strict cultural practices to control PVY infection. These methods include isolating plants from sources of infection, wide spacing to avoid plant contact, and the use of insecticides to control aphid populations. Additionally, fields must be visually inspected for morphological signs of infection; plants showing visible signs of PVY infection are destroyed by the grower. Because most of the commercial potato cultivars are propagated vegetatively, maintaining virus-free lines is of critical importance to the potato grower. Farmers plant 'potato seeds', which are not actually true seeds, but rather pieces of potato tubers. Before 'potato seeds' can be sold to the farmer, they must pass a rigorous series of tests to be certified virus free. PVY infection of 'potato seeds' is a cause of seed decertification. Commercially important potato cultivars to which the present invention may be applied include but are not limited to Russet Burbank, Shepody, Atlantic, Norchip, and Superior.

The PVY genomic RNA replicates through RNA intermediates in a DNA-independent fashion. PVY RNA has one open reading frame (ORF) that codes for a polyprotein of 352 kilodaltons (kDa). This polyprotein undergoes proteolytic processing by viral encoded proteases and a host protease to yield around or about eight viral proteins of 31 kDa, 62 kDa, 38 kDa, 71 kDa, 5.6 kDa, 50 kDa, 60 kDa, and 30 kDa. These proteins can be found in the infected plant cell and form the necessary components for viral replication. The 60 kDa viral encoded protein known as the nuclear inclusion II or nuclear inclusion B protein (also referred to as replicase) is believed to function in the replication of the viral RNA.

In general, a replicase gene derived from a particular potyvirus shares certain common features with replicase genes derived from other potyviruses. One of these common features is the location of the gene within the potyviral genome. The replicase gene is typically located directly upstream from the potyviral coat protein. A second common feature is that there is a defined type of cleavage site with a consensus sequence, which is processed by the potyviral protease during cleavage of the polyprotein. Yet a third common feature is the presence of the GDD domain in potyviral replicases, which was discussed earlier herein with regards to two replicases from the alfalfa mosaic virus. The GDD domain is thought to be involved in catalytic function and is typically found in proteins capable of replicating nucleic acids (Hodgman, 1981). A fourth common feature is the relatedness of the overall sequence of the potyviral replicase with other known replicase genes. [See Riechmann et al., *Journal of General Virology,* (1992) 73: 1–16; and Garcia et al., *Virology,* (1992) 188: 697–703].

In the course of a potyviral infection, the replicase (60 kDa) protein and the protease protein (50 kDa, also referred to as the nuclear inclusion I or nuclear inclusion A protein) are posttranslationally transported across the nuclear membrane into the nucleus of the plant cell at the later stages of viral infection and accumulate to high levels. Generally speaking, transport across the nuclear envelope is an active process mediated by a nuclear localization signal (NLS) contained within the primary sequence of the transported protein. Unlike classical signal sequences, which are generally located at the N-terminus, nuclear localization signals may be found at any site within the protein, including the N-terminus. Nuclear localization signals have been identified as sequences that may by genetic or biochemical fusion render a cytoplasmic protein nuclear, or when deleted or mutated, may no longer promote nuclear uptake of the protein in which they reside.

NLSs are typically short sequences (8–10 amino acids), contain a high proportion of positively charged amino acids (lysine and arginine), are not located at specific sites within the protein, are not removed following localization, and can occur at more than one site within the protein. Nuclear localization signals may interact with the nuclear pore complex or, possibly, cytoplasmic components. [See Garcia-Bustos et al. (1991) for a recent discussion of nuclear protein localization]. Here, the accumulation of the potyvirus replicase in the nucleus at later stages of infection indicates that the presence of replicase in the cytoplasm of the cell at that phase may actually interfere with some aspect of viral assembly. Although not fully understood, the over-accumulation of the potyvirus replicase in the cytoplasm of the plant cell by the over-expression of the protein, or the prevention of nuclear localization at a particular stage in the viral replication may be the mechanism by which resistance to the potyvirus is conferred to the transformed plant. Alternate means by which this resistance could be conferred include the binding of the viral RNA by the replicase and subsequent transport of the complex to the nucleus; binding of the viral RNA and prevention of its assemby into viral particles; or a disturbance of the balance between various required components and subsequent interference with the assembly of an active enzyme complex.

As can be seen from the foregoing discussion, potyviral infection of various plants is a serious problem encountered in agriculture today. Thus, it would be a significant contribution to the art to develop an alternative method to those currently available that is effective for conferring viral resistance to plants.

SUMMARY OF THE INVENTION

It is an object of the present invention to provide an isolated DNA molecule encoding a potyvirus replicase.

It is another object of this invention to provide a DNA molecule which comprises:

(a) a promoter region which functions in plant cells to cause the production of an RNA sequence; which is operably linked to (b) a structural gene encoding a potyvirus replicase; which is operably linked to (c) a 3' non-translated DNA sequence which functions in plant cells to cause the termination of transcription and the addition of polyadenylated ribonucleotides to the 3' end of the transcribed mRNA sequence.

It is yet another object of the present invention to provide a method for providing resistance to infection by a potyvirus in a susceptible plant which comprises:

(a) transforming plant cells with a DNA molecule encoding a replicase from a potyvirus which is capable of infecting said plant;

(b) regenerating said plant cells to provide a differentiated plant; and (c) selecting a transformed plant which expresses the potyvirus replicase gene at a level sufficient to render the plant resistant to infection by said potyvirus.

Yet another object of the present invention is to provide a method for providing resistance to infection by a potyvirus in a susceptible Solanaceae plant which comprises:

(a) transforming Solanaceae plant cells with a DNA molecule encoding a replicase from a potyvirus which is capable of infecting said Solanaceae plant;

(b) regenerating said plant cells to provide a differentiated plant; and (c) selecting a transformed Solanaceae plant which expresses the potyvirus replicase gene at a level sufficient to render the plant resistant to infection by said potyvirus.

It is a further object of the present invention to provide a virus resistant transformed plant which contains a potyvirus replicase gene.

It is still a further object of the present invention to provide virus resistant transformed plant cells which contain a potyvirus replicase gene.

Figure 1:
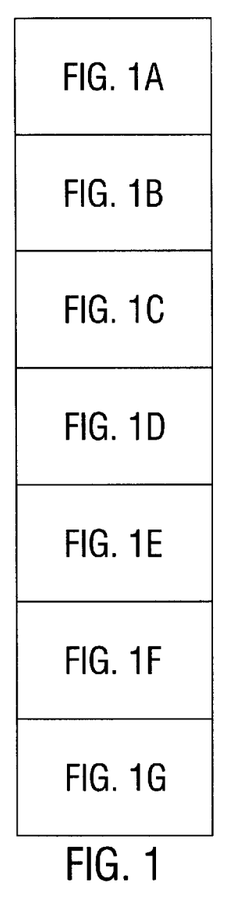
FIG. 1 illustrates the cDNA sequence (SEQ ID NO.1) and the predicted amino acid sequence of a PVY genomic clone that includes the replicase gene sequence.
Figure 1A:
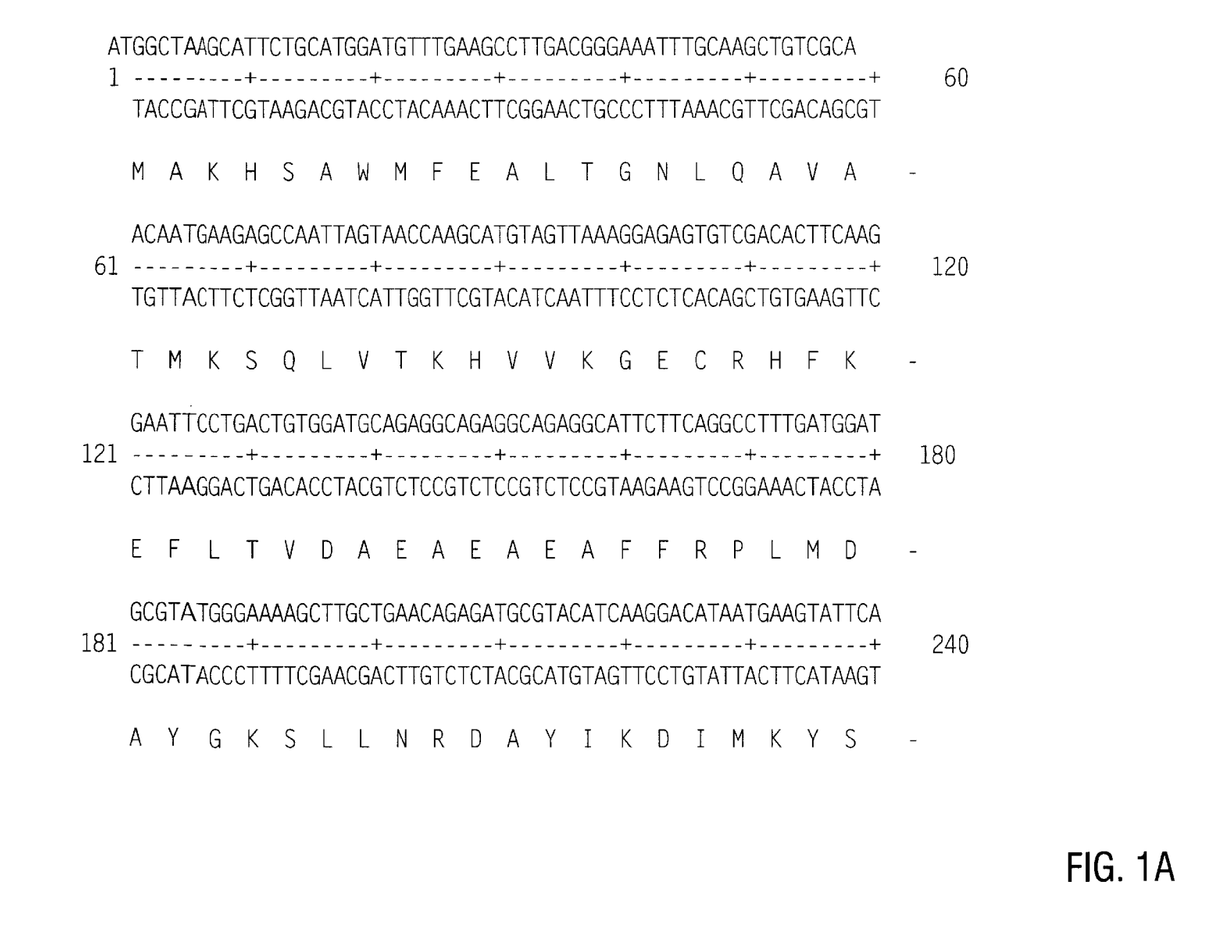
Figure 1B:
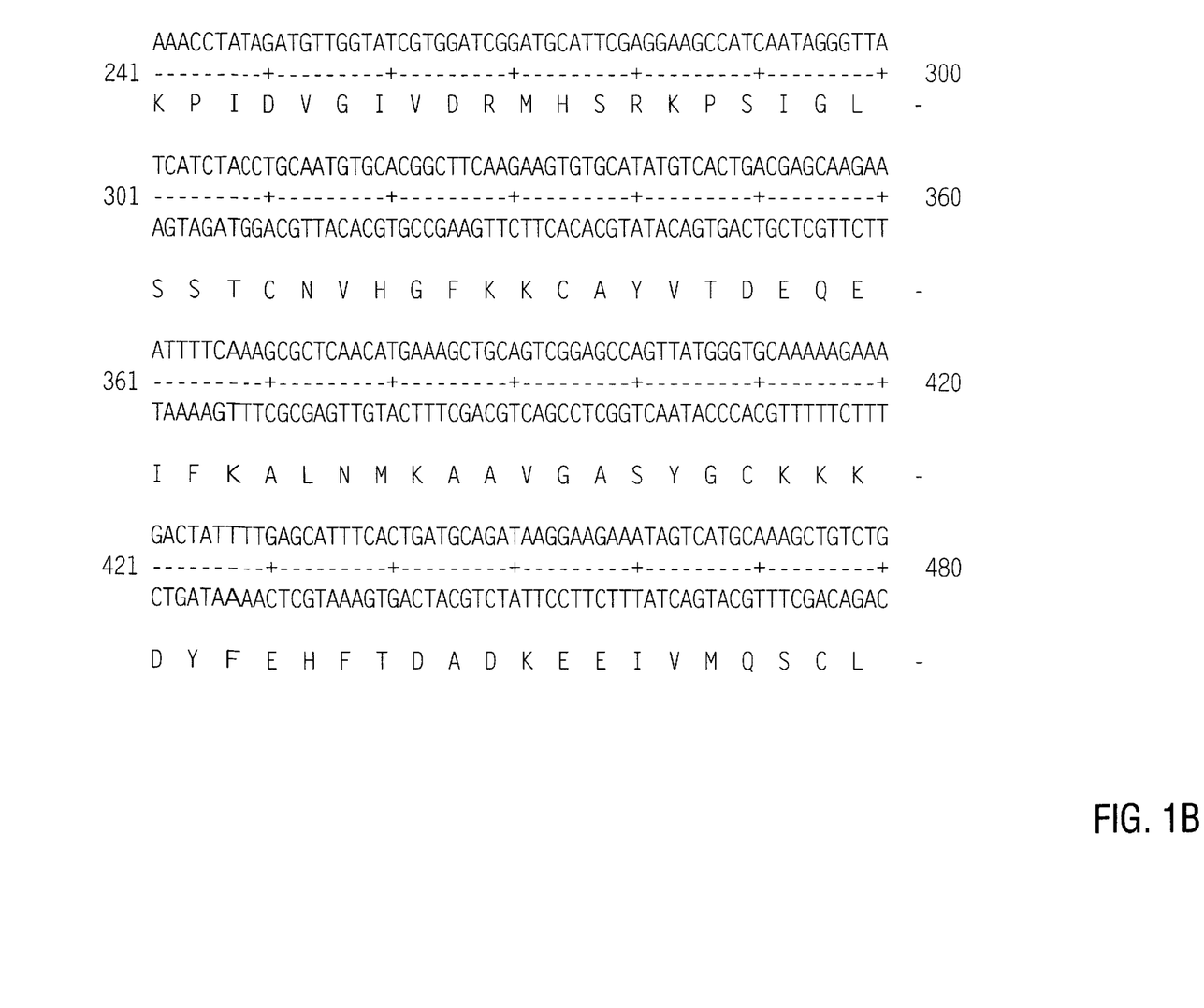
Figure 1C:
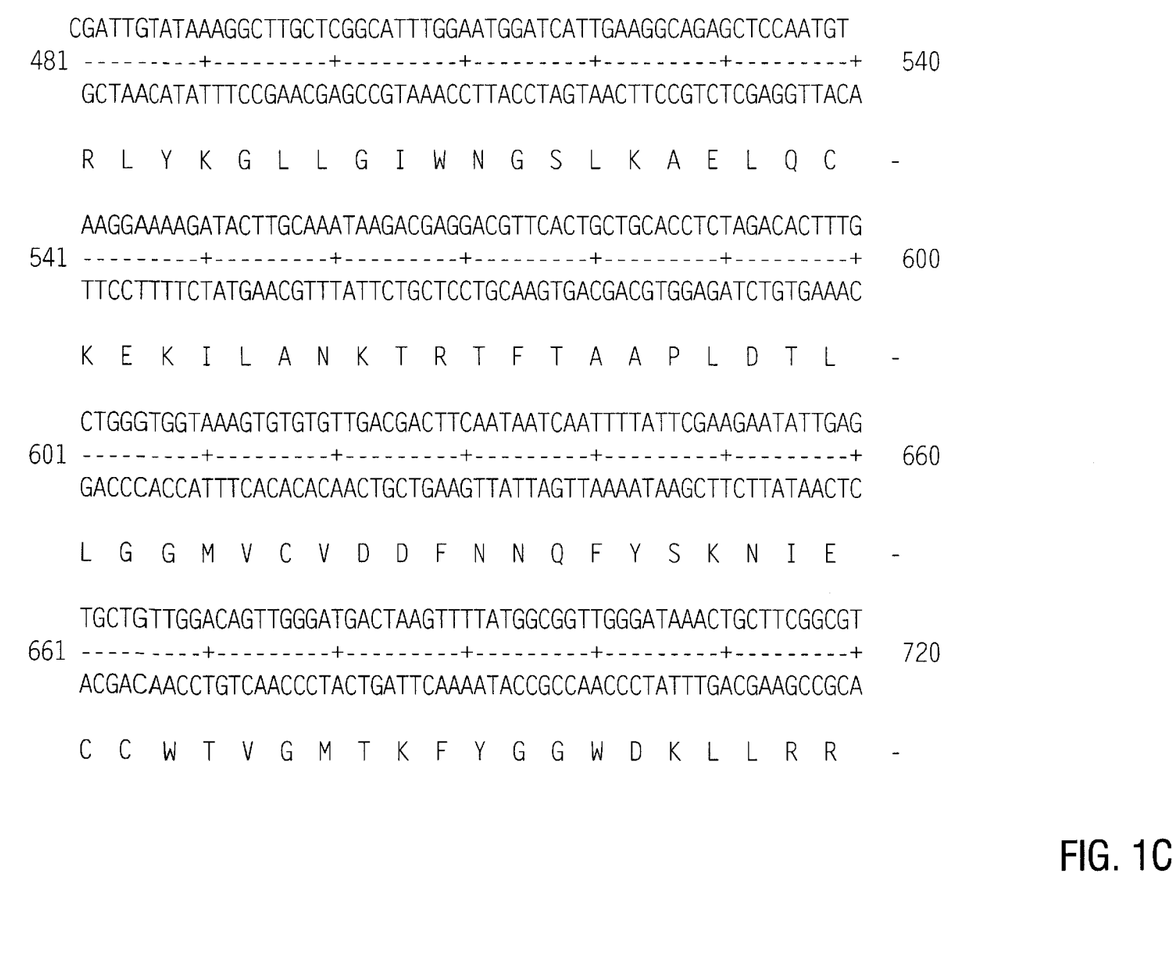
Figure 1D:
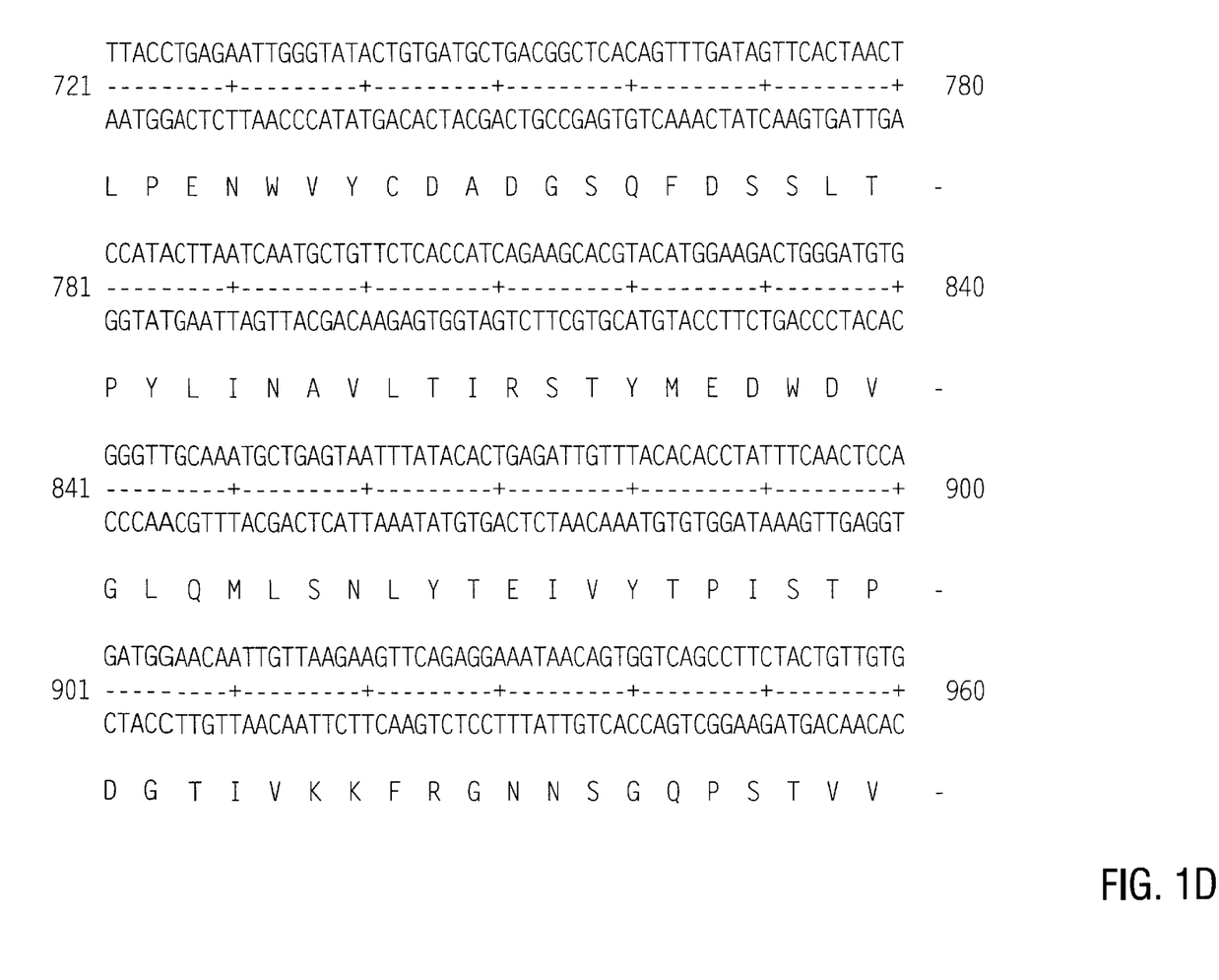
Figure 1E:
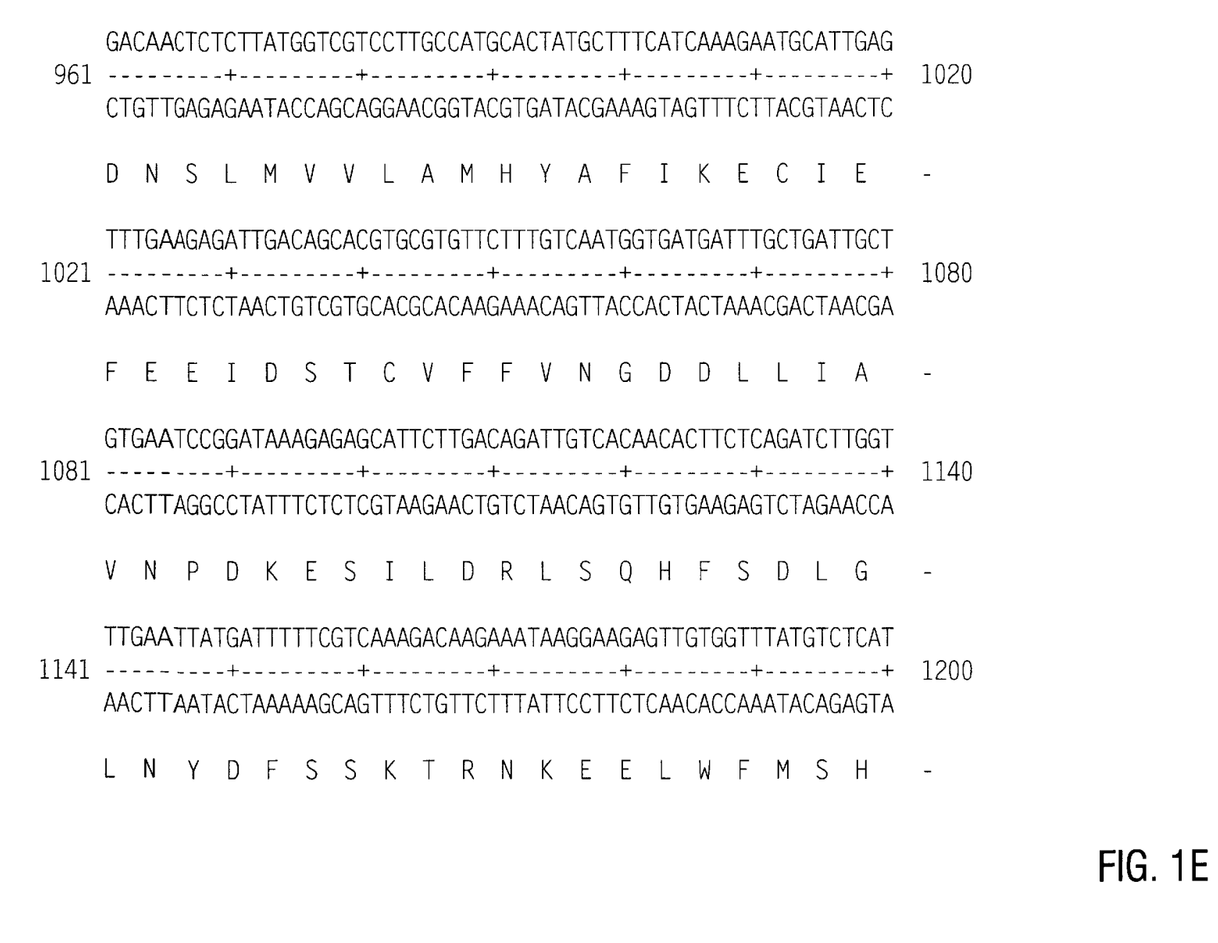
Figure 1F:
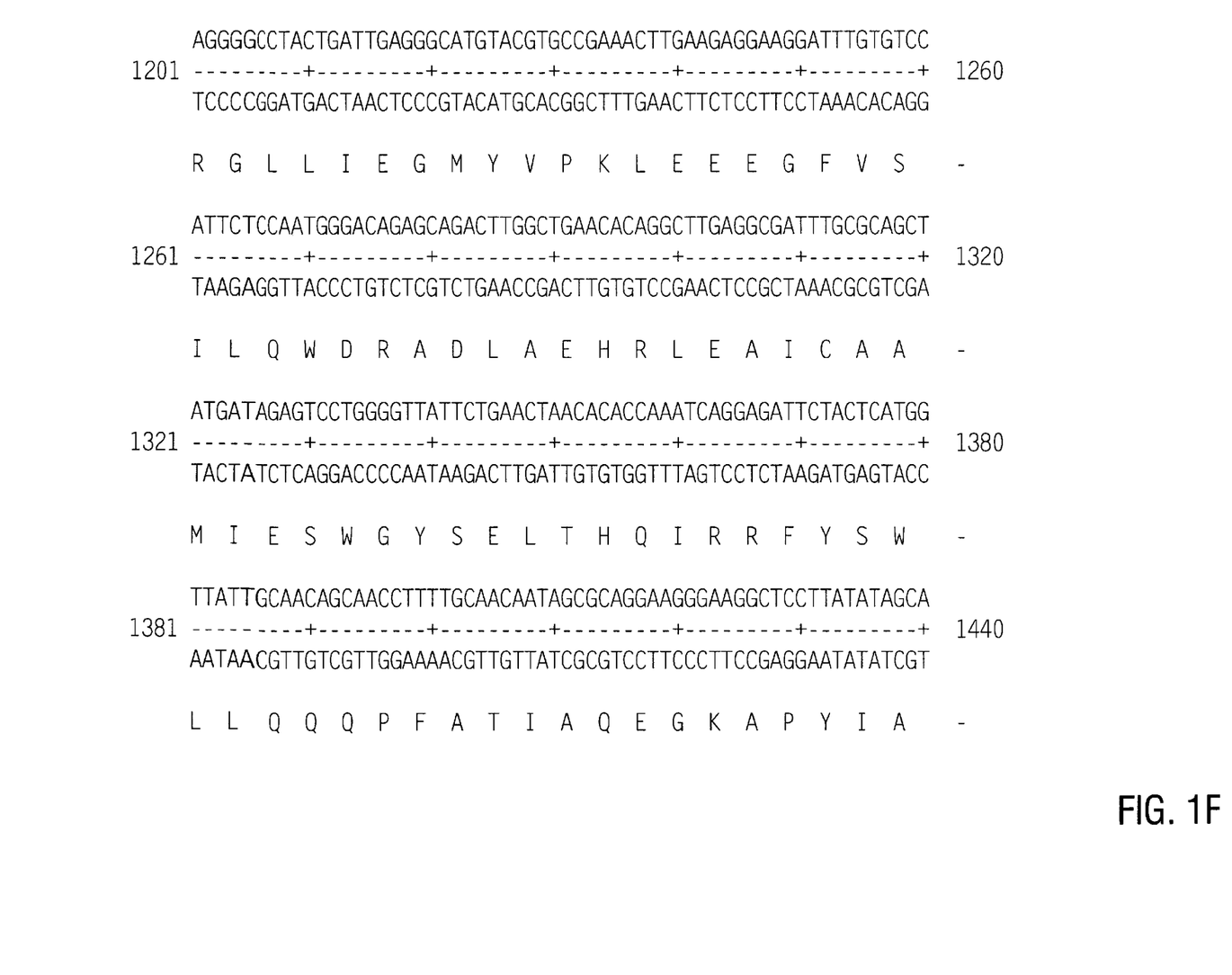
Figure 1G:
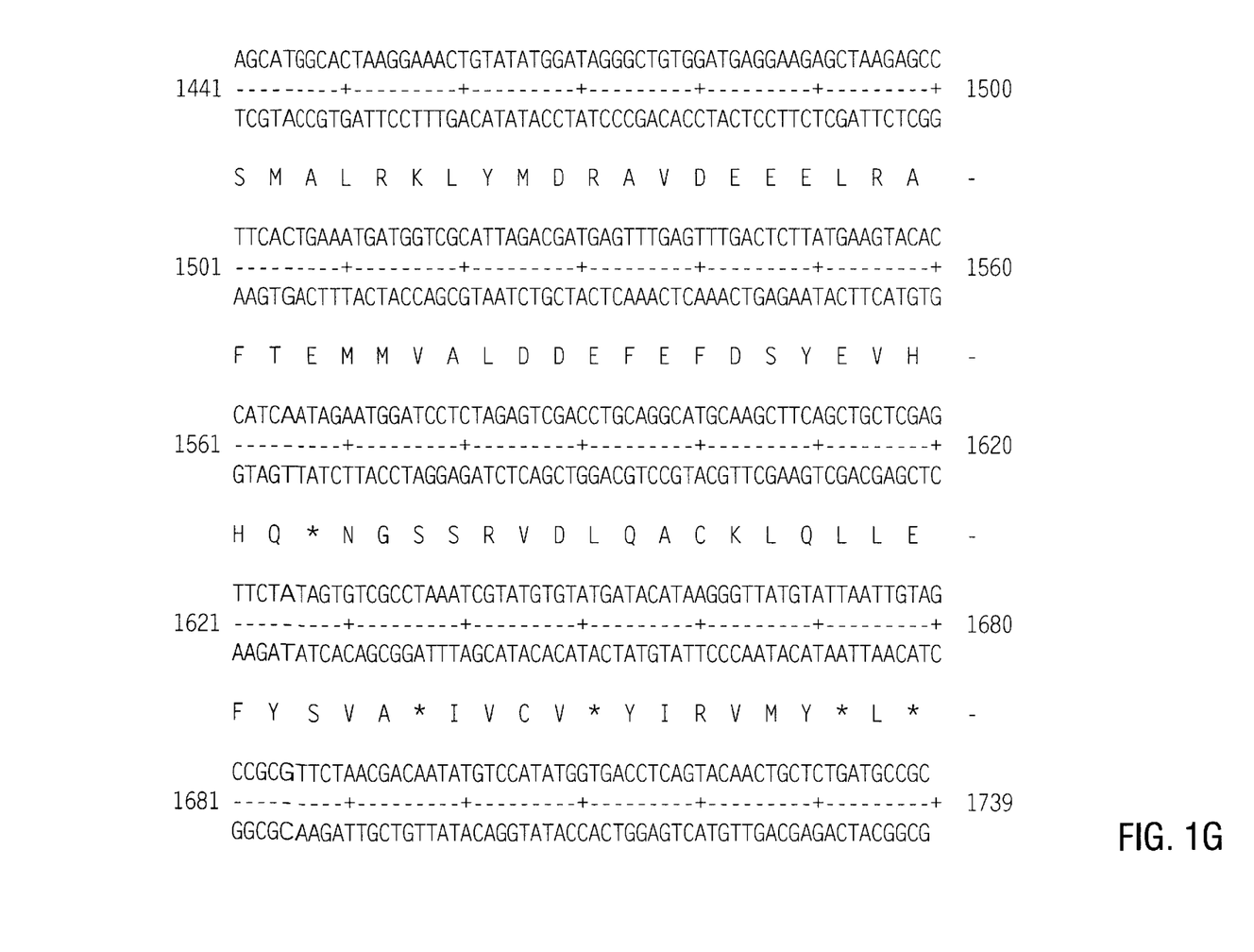

A still further object of the present invention is to provide potato tubers which contain the DNA molecule as shown in FIG. 1.

Other objects, aspects, and advantages of the present invention will be apparent to those skilled in the art from the following description, examples, and claims.

BRIEF DESCRIPTION OF THE DRAWINGS

FIG. 2 illustrates a physical map of the plasmid pMON17227.

FIG. 3 illustrates a physical map of the plasmid of pMON18678.

FIG. 4 illustrates the DNA sequence of the full-length transcript promoter region from figwort mosaic virus (SEQ ID NO. 4).

DETAILED DESCRIPTION OF THE INVENTION

The viral resistance conferred to plants of the present invention is provided by the expression in planta of an isolated DNA sequence comprising nucleotides encoding a potyvirus replicase. Suitable potyviruses from which the replicase gene may be isolated include but is not limited to potato virus Y (PVY), tobacco vein mottling virus, watermelon mosaic virus, zucchini yellow mosaic virus, bean common mosaic virus, bean yellow mosaic virus, soybean mosaic virus, peanut mottle virus virus, beet mosaic virus, wheat streak mosaic virus, maize dwarf mosaic virus, sorghum mosaic virus, sugarcane mosaic virus, johnsongrass mosaic virus, plum pox virus, tobacco etch virus, sweet potato feathery mottle virus, yam mosaic virus, and papaya ringspot virus. For the sake of clarity and brevity of explanation, the following description of the particular embodiments will be exemplified by the use of potato virus Y (PVY).

A PVY genome may be isolated from a cDNA library made from RNA recovered from purified PVY virions. The cDNA library may be constructed in a number of ways known to those of skill in the art. The cDNA sequence of an exemplary replicase gene derived from the exemplified PVY isolate is 1569 nucleotides in length and is illustrated in FIG. 1. The PVY replicase coding region is designated as SEQ ID NO: 1. The deduced amino acid sequence is shown below the cDNA sequence in FIG. 1.

This PVY replicase cDNA sequence was the source used to produce the replicase DNA sequences of this invention. The nucleotide sequence of the replicase gene may be modified at the 5' and 3' ends to facilitate cloning. This may be accomplished by site-directed mutagenesis, using the method described by Kunkel (1985), and may provide different restriction sites as needed. Various oligonucleotide primers may be used to modify the 5' and 3' ends. For example, the structural gene of the present invention (replicase) was engineered in such a way as to introduce a methionine residue at the N-terminus. This was done to facilitate the initiation of translation. Since the replicase gene is normally a part of a larger polyprotein which is proteolytically processed in the host cell in order to release the various proteins coded for by the potyvirus, the replicase gene would not normally contain the AUG initiation codon. The same type of manipulation was performed on the poliovirus protease gene, with a methionine residue introduced at the N-terminus. The poliovirus protease gene is also a part of a larger polyprotein which is proteolytically cleaved into its various components, and does not normally contain an initiation codon. The resulting protease containing the N-terminal methionine was shown to be functional. [Ivanoff et al., *Proc. Nat'l Acad. Sci.* 83: 5392–5396 (1986)]. A representative protocol is outlined in the Example.

Sequencing of the replicase gene was performed by the method of Sanger and Coulson, *Proc. Nat'l Acad. Sci.* 74: 5463–5467 (1977) using a Sequenase® product, according to the manufacturer's instructions. In this and all amino acid sequences herein, the standard single letter nomenclature is used (see Table 2 below). All peptide structures represented in FIG. 1 are shown in conventional format wherein the amino group at the N-terminus appears at the left and the carboxyl group at the C-terminus at the right.

TABLE 2

Abbreviations for amino acids

| Amino acid | One-letter symbol |
| --- | --- |
| alanine | A |
| arginine | R |
| asparagine | N |
| aspartic acid | D |
| asparagine or aspartic acid | B |
| cysteine | C |
| glutamine | Q |
| glutamic acid | E |
| glutamine or glutamic acid | Z |
| glycine | G |
| histidine | H |
| isoleucine | I |
| leucine | L |
| lysine | K |
| methionine | M |
| phenylalanine | F |
| proline | P |
| serine | S |
| threonine | T |
| tryptophan | W |
| tyrosine | Y |
| valine | V |

It is understood that the particular nucleotide and/or amino acid sequences disclosed in FIGS. 1 and 4 are representative in the sense that equivalent genes or portions thereof may be obtained and/or generated pursuant to this disclosure. By equivalent it is meant that said gene or portion thereof would function in a manner substantially the same as the replicase gene disclosed herein, and would provide viral resistance to a plant in substantially the same manner.

A structural DNA sequence encoding the viral replicase gene may be inserted into a plant transformation vector. A gene is defined as an element or combination of elements that are capable of being expressed in a cell, either alone or in combination with other elements. In general, a gene comprises (from the 5' to the 3' end): (1) a promoter region which includes a 5' non-translated leader sequence capable of functioning in plant cells; (2) a structural gene or structural DNA sequence which codes for the desired protein; and (3) a 3' non-translated region, which typically causes the termination of transcription and the polyadenylation of the 3' region of the RNA sequence. Each of these elements is operably linked to the adjacent element. A gene comprising the above elements may be inserted by standard recombinant DNA methods into a plant transformation vector. Some or all of the elements of the gene may be present, with additional or remaining elements added to the vector if necessary. A further aspect of the present invention is the introduction of multiple copies of the replicase gene into the plant cell. Additionally, the plant transformation vector may be constructed with all of the elements present except for the structural gene, which may then be added at an appropriate time by known methods.

The segment of DNA referred to as the promoter is responsible for the regulation of the transcription of DNA into mRNA. A number of promoters which function in plant cells are known in the art and may be employed in the practice of the present invention. These promoters may be obtained from a variety of sources such as plants or plant viruses, and may include but are not limited to promoters isolated from the caulimovirus group such as the cauliflower mosaic virus 35S promoter (CaMV35S), the enhanced cauliflower mosaic virus 35S promoter (enh CaMV35S), the figwort mosaic virus full-length transcript promoter (FMV35S), and the promoter isolated from the chlorophyll a/b binding protein. The DNA sequence of an exemplary FMV35S promoter is presented in FIG. 5 and is identified as SEQ ID NO. 4. Other useful promoters include promoters which are capable of expressing the replicase enzyme in an inducible manner or in a tissue-specific manner in certain cell types in which the infection is known to occur. For example, the inducible promoters from phenylalanine ammonia lyase, chalcone synthase, hydroxyproline rich glycoprotein, extensin, pathogenesis-related proteins (e.g. PR-1a), and wound-inducible protease inhibitor from potato would be useful.

Alternate promoters, such as the promoter from glutamine synthetase for expression in vascular tissues or promoters from epidermal cells, could be used to express the protein in certain cell types. The patatin promoter could be used to express the protein in the tuber. The particular promoter selected is preferably capable of causing sufficient expression of the replicase structural gene to which it is operably linked to result in the production of an effective amount of the replicase enzyme to provide viral resistance, but not so much as to be detrimental to the cell in which it is expressed. The promoters selected should be capable of functioning in tissues including but not limited to epidermal, vascular, and mesophyll tissues. The actual choice of the promoter is not critical, as long as it has sufficient transcriptional activity to accomplish the expression of the replicase gene and subsequent conferral of viral resistance to the plants.

The non-translated leader sequence can be derived from any suitable source and can be specifically modified to increase the translation of the mRNA. The 5' non-translated region can be obtained from the promoter selected to express the gene, the native leader sequence of the gene or coding region to be expressed, viral RNAs, suitable eucaryotic genes, or a synthetic gene sequence. The present invention is not limited to the construct presented in the following example. The non-translated leader sequence can also be derived from an unrelated promoter or viral coding region as described.

The structural DNA sequence which codes for the replicase may be isolated from any potyvirus using methods known to those of skill in the art as discussed earlier in this section. Modifications to this gene may also be made, including modifications to the 5' or 3' termini of the structural gene, such as the introduction of an initiation codon at the 5' end. Additional modifications that could foreseeably be made to this structural DNA sequence encoding replicase include but are not limited to those modifications which would alter the GDD domain, or the nuclear location sequence (NLS), both of which are contained within the replicase coding region. In particular, modifying the NLS would presumably alter the ability of the replicase to enter the nucleus, thus accumulating in the cytoplasm of the plant cell. This scenario was one of the postulated mechanisms discussed earlier herein of how viral resistance was conferred to the transformed plant cell by way of the present invention.

The termination region or 3' non-translated region which is employed is one which will cause the termination of transcription and the addition of polyadenylated ribonucleotides to the 3' end of the transcribed mRNA sequence. The termination region or 3' non-translated region will be additionally one of convenience. The termination region may be native with the promoter region, native with the structural gene, or may be derived from another source, and preferably include a terminator and a sequence coding for polyadenylation. Suitable 3' non-translated regions of the chimeric plant gene include but are not limited to: (1) the 3' transcribed, non-translated regions containing the polyadenylate signal of Agrobacterium tumor-inducing (Ti) plasmid genes, such as the nopaline synthase (NOS) gene, and (2) plant genes like the soybean 7S storage protein genes and the pea small subunit of the ribulose 1,5-bisphosphate carboxylase-oxygenase (ssRUBISCO) E9 gene.

In developing the expression construct, the various components of the expression construct or fragments thereof will normally be inserted into a convenient cloning vector which is capable of replication in a bacterial host, such as *E. coli*. Numerous vectors exist that have been described in the literature. After each cloning, the vector may be isolated and subjected to further manipulation, such as restriction, insertion of new fragments, ligation, deletion, resection, insertion, in vitro mutagenesis, addition of polylinker fragments, and the like, in order to provide a vector which will meet a particular need. Once the construct is completed, it may then be transferred to an appropriate vector for further manipulation in accordance with the manner of transformation of the plant cell.

A variety of techniques are available for the introduction of the genetic material into or transformation of the plant cell host. However, the particular manner of introduction of the plant vector into the host is not critical to the practice of the present invention. Any method which provides for efficient transformation may be employed. In addition to transformation using plant transformation vectors derived from the tumor-inducing (Ti) or root-inducing (Ri) plasmids of Agrobacterium, alternative methods could be used to insert the DNA constructs of the present invention into plant cells. Such methods may include, for example, the use of liposomes, electroporation, chemicals that increase the free uptake of DNA, DNA delivery via microprojectile bombardment, microinjection, and transformation using viruses or pollen.

A plant transformation vector preferably includes all of the necessary elements for transformation of plant cells. Typical plant cloning vectors comprise selectable marker genes, scoreable marker genes, T-DNA borders, cloning sites, appropriate bacterial genes to facilitate the identification of transformants, broad host range replication and mobilization functions, and other elements as desired. The replicase gene can be inserted into any suitable plant transformation vector for transformation into the desired plant species. Suitable plant transformation vectors include those derived from a Ti plasmid of *Agrobacterium tumefaciens*, in addition to those disclosed, for example, by Herrera-Estrella (1983), Bevan (1984), Klee (1985) and U.S. Pat. No. 4,940,838, issued to Schilperoort et al.

Selectable marker genes may be used to select for those cells which have become transformed. Conveniently, the marker employed may be resistance to an antibiotic, such as kanamycin, gentamycin, G418, hygromycin, streptomycin, spectinomycin, tetracycline, chloramphenical, and the like. Other markers could be employed in addition to or in the alternative, such as, for example, a gene coding for herbicide tolerance such as tolerance to glyphosate, sulfonylurea, phosphinothricin, or bromoxynil. Additional means of selection could include resistance to methotrexate, heavy metals, complementation providing prototrophy to an auxotrophic host, and the like. The particular marker employed will be one which will allow for the selection of transformed cells as opposed to those cells which were not transformed. Depending on the number of different host species one or more markers may be employed, where different conditions of selection would be used to select the different host, and would be known to those of skill in the art.

Plant transformation vectors containing the PVY replicase gene may be used to transform plants of the Solanaceae family. In particular, infection by PVY is a persistent problem in potato and can infect tomato and tobacco. An Agrobacterium-mediated transformation protocol is known to be effective in transforming members of the Solanaceae family. When an Agrobacterium-mediated transformation is used, the desired transformation vector is mobilized into a suitable Agrobacterium strain. The ABI Agrobacterium strain is described for exemplary purposes. The desired transformation vector is mobilized into an ABI Agrobacterium strain by the triparental mating system using the helper plasmid pRK2013 (Ditta et al. 1980). The binary ABI strain is the chloramphenicol resistant derivative of *Agrobacterium tumefaciens* A208 which carries the disarmed Ti plasmid pTiC58 (Koncz and Schell 1986). The Ti plasmid does not carry the T-DNA phytohormone genes and the strain is therefore unable to cause crown gall disease. The disarmed Ti plasmid provides the trfA gene functions required for autonomous replication of the vector after conjugation into the ABI strain. When the plant tissue is incubated with the ABI::transformation vector conjugate, the vector is transferred to the plant cells by the vir functions encoded by the disarmed pTiC58 plasmid. The pTiC58 Ti plasmid does not transfer to the plant cells, but remains in the Agrobacterium. Either single- or double-border transformation vectors can be delivered to the plant by Agrobacterium. Single border vectors open at the right T-DNA border region, and the entire vector sequence is inserted into the host plant chromosome. The right border is lost during transfer and integration. In a double border vector, DNA between the right and left borders is inserted into the plant chromosome, thereby delivering only the chimeric genes of interest to the chromosome. The remainder of the vector, and the border sequences are lost during the transfer and integration.

Transformation and regeneration protocols for members of the Solanaceae family are known. In particular, various transformation and regeneration protocols for potato and tomato have been established. An exemplary protocol for potato is described in the Example. Additionally, potato may be transformed in the following manner. Agrobacterium containing the desired plant transformation vector is grown overnight in 2 mls of LBSCK broth. LBSCK contains 10 g NaCl, 5 g yeast extract, 10 g Bacto-Tryptone, 50 mg spectinomycin, 25 mg chloramphenicol and 50 mg kanamycin in a 1 liter volume, pH 7.0. The following day, the bacteria are diluted 1:10 with MSO or until an OD (optical density) reading of 0.2–0.3 is established. MSO contains 4.4 g MX salts (Sigma Chemical Co., St. Louis, Mo.), 30 g sucrose and 2 ml $B_5$ vitamin (500×) in a 1 liter volume, pH 5.7. Leaves from the stem of potato plants that have been grown under sterile conditions for about three (3) weeks on PM media supplemented with 25 mg/l ascorbic acid are removed. PM media contains 4.4 g MS salts (Sigma Chemical Co., St. Louis, Mo.), 30 g sucrose, 0.17 g $NaH_2PO_4.H_2O$, 1 ml thiamine HCl and 0.1 g Inositol in a 1 liter volume, pH 6.0 and 0.2% Gelrite agar. The stems are placed on a vegetable slicer (~30–50 at a time) and cut into 3–5 mm segments. These stem explants are inoculated for 15 minutes with the diluted bacteria. Approximately 20 mls of bacterial solution is used per 1000 stem explants. The bacterial solution is removed by aspiration and the explants placed onto prepared co-culture plates. The co-culture plates contain 1/10 MSO with 1.5 mls of TxD cells overlayed with wetted filter paper. Approximately 50 explants are placed on each plate.

After a two day co-culture period, explants are placed onto callus induction plates containing MSO plus 0.5 mg/l ZR (Zeatin riboside), 10 mg/l $AgNO_3$ and 0.1 mg/l NAA (naphthaleneacetic acid) for four (4) weeks. These plates also contain 100 mg/l kanamycin to select for transformed cells. After four (4) weeks, explants that exhibit growth in the presence of kanamycin are placed on shoot induction media which contains MSO plus 5.0 mg/l ZR, 10 mg/l $AgNO_3$ and 0.3 mg/l $GA_3$ (gibberellic acid) and 100 mg/l kanamycin for further selection. Shoots typically begin to appear at about six (6) weeks. The plants are then placed in sundae cups with PM media and allowed to grow for approximately 2 weeks. Plants are placed into soil, hardened off, and analyzed to verify transformation by assaying for the presence of a protein which confers resistance to the antibiotic kanamycin to the plant. If the plant is positive for expression of the protein, the plant is kept for further study and maintained in tissue culture.

Alternatively, the explants may be placed on callus induction plates containing MSO plus 3.0 mg/l BA (6-benzylaminopurine) and 0.01 mg/l NAA for four (4) weeks with 100 mg/l kanamycin for selection. For shoot induction, the explants are placed on MSO plus 0.3 mg/l $GA_3$ only and 100 mg/ml kanamycin for selection. Shoots begin to appear at about 8 weeks. Shoots are recallused on MSP-5 with 200 mg/ml kanamycin and assayed in two weeks. MSP-5 contains 4.4 g MS salts (Sigma), 5 ml SLLX vitamins (200×), 30 g sucrose, 2.25 ml BAP, 0.186 ml NAA in 1 liter, pH 5.6 and 0.2% Gelrite agar.

After the potato plant has been transformed and after transformed callus has been identified, the transformed callus tissue is regenerated into whole plants. Any known method of regeneration of potato plants can be used in this invention.

For tomato, the transformation protocol described in McCormick et al. (1986) can generally be used The regeneration of plants from either single plant protoplasts or various explants is well known in the art. See, for example, *Methods for Plant Molecular Biology,* A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. The regeneration of plants transformed by Agrobacterium from leaf explants can be achieved as described by Horsch et al., *Science* 227:1229–1231 (1985). In this procedure, transformants are grown in the presence of of a selection agent and in a medium that induces the regeneration of shoots in the plant species being transformed as described by Fraley et al., *Proc. Nat'l. Acad. Sci. U.S.A.,* 80:4803 (1983). This procedure typically produces shoots within 2 to 4 months and these transformant shoots are then transferred to an appropriate root-inducing medium containing the selective agent and an antibiotic to prevent bacterial growth. Transformant shoots that are rooted in the presence of the selective agent to form plantlets are then transplanted to soil or other media to allow the production of roots. These procedures vary depending on the particular plant species employed, such variations being well known in the art A plant of the present invention containing the desired replicase gene is cultivated using methods known to those of skill in the art. A transformed plant of the present invention thus is capable of expressing the replicase gene and exhibits viral resistance thereby. The presence of the replicase gene or gene product in the transformed plant may be determined by any suitable method known to those of skill in the art. Included in these methods are Southern, Northern, and Western Blot techniques, ELISA, and various bioassays. The transformed plant capable of expressing replicase may then be assayed for the determination of antiviral activity. A representative assay to accomplish this is included in the Example.

The following Example is provided to better elucidate the practice of the present invention and should not be interpreted in any way as to limit the scope of the present invention. Those skilled in the art will recognize that various modifications can be made to the methods and genes described herein while not departing from the spirit and scope of the present invention. For the sake of clarity and brevity of explanation, the following description of the particular embodiments will be exemplified by the use of potato virus Y (PVY).

EXAMPLE

General information pertinent to the Example:
Strains and Plasmids
*E. coli* strain MV 1190 (from Biorad)
Agrobacterium strain ABI
helper plasmid pRK2013
pMON17227
pMON18678
TxD cells
Media, Buffers, and Solutions LBSCK contains 10 g NaCl, 5 g yeast extract, 10 g Bacto-Tryptone, 50 mg spectinomycin, 25 mg chloramphenicol and 50 mg kanamycin in a 1 liter volume, pH 7.0.

MSO contains 4.4 g MX salts (Sigma Chemical Co., St. Louis, Mo.), 30 g sucrose and 2 ml $B_5$ vitamin (500×) in a 1 liter volume, pH 5.7.

PM media contains 4.4 g MS salts (Sigma Chemical Co., St. Louis, Mo.), 30 g sucrose, 0.17 g $NaH_2PO_4.H_2O$, 1 ml thiamine HCl and 0.1 g inositol in a 1 liter volume, pH 6.0 and 0.2% Gelrite agar.

shoot induction media contains MSO plus 5.0 mg/l ZR, 10 mg/l $AgNO_3$ and 0.3 mg/l $GA_3$ (gibberellic acid) and 100 mg/l kanamycin.

callus induction plates contains MSO plus 3.0 mg/l BA (6 benzylaminopurine) and 0.01 mg/l NAA.

callus induction media contains 5 mg/l Zeatin Riboside, 10 mg/l $AgNO_3$, and 0.1 mg/l NAA.

NAA is naphthaleneacetic acid.

Davis germination media contains 4.3 g/l MS salts, 20 g/l sucrose and 10 mls/l Nitsch vitamins, pH 5.8.

Davis regeneration media contains 1× MS salts, 3% sucrose, 1× Nitsch vitamins, 2.0 mg/l zeatin, pH 5.8.

Nitsch vitamin solution contains 100 mg/l myo-inositol, 5 mg/l nicotinic acid, 0.5 mg/l pyridoxine HCl, 0.5 mg/l thiamine HCl, 0.05 mg/l folic acid, 0.05 mg/l biotin, 2 mg/l glycine.

MSP-5 contains 4.4 g MS salts (Sigma), 5 ml SLLX vitamins (200×), 30 g sucrose, 2.25 ml BAP, 0.186 ml NAA in 1 liter, pH 5.6 and 0.2% Gelrite agar.

LB media contains 10 g tryptone, 5 g yeast extract and 5 g NaCl per liter; optionally with 25 µg/ml chloramphenicol and 50 mg kanamycin.

Unless otherwise specified, the above solutions represent the basic (1×) concentration employed. Throughout the Examples, where different concentration levels are employed, that fact is indicated by referring to the solution as a multiple of the basic (1×) concentration.

Construction of the Potyvirus cDNA Library

PVY virus particles were isolated from systemically infected Samsun tobacco plants 14 days post inoculation (DPI) based on methods by Yang et al, 1983 (Yang, L., Reddick, B. and Slack, S. A. 1983. Phytopathology 73:794) and Baum and Barnett, 1981 (Baum, R. H., and Barnett, O. W., 1981, Phytopathology 71:1981). Viral RNA was prepared by incubating the isolated virus particles in 100 mM Tris, pH 7.5, 0.5% sodium dodecyl sulfate (w/v), and 0.1 mg/ml proteinase K for 30 minutes at 37° C. The virus solution was then extracted with phenol twice and then precipitated in 0.1 volumes of 3 M sodium acetate, pH 4.0, and two volumes of absolute ethanol. The resulting pellet following precipitation was suspended in 10 mM Tris, pH 8.0 and 1 mM EDTA.

cDNA was prepared from this RNA using the cDNA Cloning System (Amersham Corporation, Arlington Heights, Ill.) according to the manufacturer's directions. The resulting cDNA was cloned into the Lambda Zap II vector (Stratagene, La Jolla, Calif.) and packaged into lambda phage according to the manufacturer's directions (Amersham Corporation, Arlington Heights, Ill.) using the in vitro packaging system for lambda DNA. The resulting cDNA library was screened using a $^{32}$P-labelled probe which corresponded to a 2577 bp Eco RI fragment of PVY cDNA. This fragment had been previously isolated from a cDNA library and contained the terminal 3' 2577 bases corresponding to the 3' end of the PVY RNA. DNA from lambda plaques which hybridized with this probe was isolated and analyzed by restriction enzyme mapping. One lambda cDNA clone contained a 6359 bp cDNA fragment corresponding to approximately the 3' two-thirds of the viral genomic RNA. This clone was selected for mutagenesis of the nuclear inclusion II coding region.

All mutagenesis reactions were carried out using the protocol of Kunkel (Kunkel, T. A., (1985), Rapid and specific site-specific mutagenesis without phenotypic selection. Proc. Nat'l. Acad. Sci. USA 82:488–492.) Two oligonucleotide primers were used to mutagenize the replicase coding region from the PVY cDNA:

Primer #1 (SEQ ID NO. 2):
5'-GATGTAGTGGTGGCCATGGCTAAGCATTCTG CATGG-3'

This primer was used in the site-specific mutagenesis procedure of Kunkel in order to introduce an Nco I site immediately upstream of the replicase coding region. The amino terminus of the replicase was then expressed as:

N-term: Met-Ala-Lys-His . . .
This mutagenesis procedure also added a methionine to the amino terminus of the replicase protein.
Primer #2 (SEQ ID NO. 3):
6'-GAAGTACACCATCAATAGAATGGATCCACAA TTGATGCAGG-3'
This primer was used in the site-specific mutagenesis procedure of Kunkel in order to introduce a BamH I site at the end of the coding region of the replicase and to introduce a strong termination codon (AUG) at the end of the replicase open reading frame of the mRNA.

Construction of pMON18678

The DNA coding sequence for the PVY replicase gene (SEQ ID NO: 1) was engineered into pMON17227, which is a double border plant transformation vector, to study its ability to confer resistance to PVY in plants expressing the replicase gene. A physical map of pMON17227 is shown in FIG. 3. A Bgl II and BamH I fragment from pMON9892 corresponding to the PVY coat protein coding region was inserted into the BamH I site of pMON19609. The resulting vector was cleaved with Nco I and BamH I and the large vector fragment isolated. An Nco I and BamH I fragment corresponding to the coding region of the replicase was then inserted into the Nco I and BamH I sites of this vector. The resulting plasmid carrying the coding region of the replicase under the control of the FMV promoter was designated as pMON18678. This vector was cleaved with Not I and the Not I fragment carrying the replicase was inserted into the Not I site of pMON17227. The resulting vector containing the PVY replicase gene was designated as pMON18678, and is illustrated in FIG. 4.

Plasmid pMON18678 contains the following DNA segments. The bacterial spectinomycin/streptomycin resistance gene (Spc/Str) (Fling et al.) is followed by the right border of the tDNA. Adjacent to the right border is the synthetic bacterial glyphosate resistance CP4 5-enolpyruvyl-3-phophoshikimate synthase (EPSPS) gene driven by the FMV35S promoter (see PCT publication WO92/04449). The CP4 gene confers glyphosate resistance to the transformants and thus the the capability of using glyphosate as the means for selecting transformants. A chloroplast transit peptide from the Arabidopsis 5-enolpyruvyl-3-phosphoshikimate synthase gene (EPSPS) is fused to the CP4 gene to target this gene to the chloroplasts. At the 3' end of the CP4 gene is the E9 3'end. This is followed by the left border of the tDNA, the origin of replication (ori-322) (Stalker et al. 1981). The next sequence contains a second chimeric gene, including PVY replicase. A 0.64 kb DNA sequence containing the FMV promoter functions as the transcriptional promoter for the following PVY replicase coding region. The chimeric gene ends with the 0.65 kb of the E9 3' region from the pea small subunit RUBISCO gene (Coruzzi et al. 1984).

Triparental Mating Procedure

Prior to transformation, *E. coli* containing pMON18678 were mated into Agrobacterium ABI by a triparental mating with the helper plasmid pRK2013 (Ditta et al. 1980). ABI is the A208 *Agrobacterium tumefaciens* strain carrying the disarmed pTiC58 plasmid pMP90RK (Koncz and Schell, 1986). The disarmed Ti plasmid provides the trfA gene functions that are required for autonomous replication of the pMON vector after the conjugation into the ABI strain. When plant tissue is incubated with the ABI::pMON conjugate, the vector is transferred to the plant cells by the vir functions encoded by the disarmed pMP90RK Ti plasmid. Agrobacterium were grown for 30 hours in LB media (10 g tryptone, 5 g yeast extract and 5 g NaCl per liter) with 25 μg/ml chloramphenicol and 50 mg kanamycin at 30° C. *E. coli* containing pRK2013 were grown overnight in kanamycin (50 μg/ml). This culture was started with several colonies. *E. coli* with pMON18678 were grown in LB with 75 μg/ml spectinomycin. After all of the cultures were grown, 4 ml of LB was added to a tube with 100 μl each of Agrobacterium ABI, pRK2013, and pMON18678. This mixture was centrifuged in a microfuge for 5 minutes and the supernatant fraction decanted. The pellet fraction was resuspended in the remaining liquid, and an aliquot was pipetted into the center of an LB plate. After overnight growth at 30° C., an aliquot of cells from this plate was streaked onto an LB plate supplemented with 75 μg/ml spectinomycin, 50 μg/ml kanamycin and 25 μg/ml chloramphenicol.

After 24–48 hours at 30° C., the plate from the triparental mating of pMON18678, pRK2013 and Agrobacterium ABI contained colonies, while the control plate from the mating of pMON18678 and ABI (without pRK2013, which is required for mobilization) did not contain colonies. After the triparental mating, 4 colonies were selected from the former plate, inoculated into a liquid culture of LB supplemented with 75 μg/ml spectinomycin, 50 μg/ml kanamycin and 25 μg/ml chloramphenicol and grown at 30° C. The presence of the PVY replicase gene was shown by restriction analysis of Agrobacterium DNA. One of the cultures verified to contain PVY replicase was used for transformation of potato.

Transformation of Potato

To transform potatoes using glyphosate as a selectable agent, Agrobacterium was grown overnight in 2 ml of LBSCK. The following day, the bacteria was diluted 1:10 with MSO or until an optical density reading of 0.2–0.33 was established. Leaves from the stems of potato plants that had been grown under sterile conditions for three weeks on PM media supplemented with 25 mg/ml ascorbic acid were removed, stems were cut into 3–5 mm segments and inoculated with diluted bacteria as described previously.

Explants were placed onto prepared co-culture plates. The co-culture plates contained 1/10 MSO with 1.5 mls of TxD cells overlayed with wetted filter paper. About 50 explants were placed per plate. After 2 days coculture period, explants were placed onto callus induction media which contains 5.0 mg/l Zeatin Riboside, 10 mg/l AgNO₃ and 0.1 mg/l NAA for 2 days. Explants were subsequently transferred onto callus induction media which contained 0.025 mM glyphosate for selection. After 4 weeks, explants were placed onto shoot induction media which contained 5.0 mg/l Zeatin Riboside+10 mg/l AgNO₃ and 0.3 mg/l GA3, with 0.025 mM glyphosate for selection. Shoots began to appear at 8 weeks. Explants were transferred to fresh shoot induction media every 4 weeks for 12 weeks. Shoots were excised and placed on PM media for about 2 weeks or until they were large enough to be placed into soil.

The transgenic plants were then assayed for the expression of PVY replicase by Northern blot or immunoblot analysis. Transgenic lines derived from transformation with pMON18678 were assayed by RNA Northern analysis (Thomas, 1980) to determine the presence of PVY replicase mRNA corresponding to the predicted mRNA transcript expected fom pMON18678. Transgenic potato plants that expressed replicase and nontransformed potato plants were propagated by cuttings and mechanically inoculated with PVY. Samples obtained at 4, 5, and 6 weeks post inoculation were assayed for the presence of PVY replicase by ELISA.

Potato Infection Experiments

At least 10 plants that expressed CP4 (EPSPS) were selected from each replicase line for PVY infection experiments. Non-transformed potato (Russet Burbank) was used as the control line, and data is provided in Table 3. Plants were grown and tested in an environmentally controlled chamber with the following parameters: a 15 hour photoperiod (250 μEinsteins) at 25° C., followed by 9 hours of darkness at 22° C. Throughout the experiment, the chamber was held at 50% relative humidity. The plants were inoculated with a 20.0 μg/ml of virus. 20 μl of inoculum, in a 0.5 M, pH 7.5 phosphate buffer, was lightly rubbed onto 2 leaves per plant that were pretreated with carborundum (a fine abrasive). This abrasive application slightly wounds the young leaves, and provides an enhanced opportunity for viral infection. Data from 5 replicase lines are shown in Table 3.

To determine the incidence of infection in inoculated lines, a #8 sized core borer, which yields circular samples weighing approximately 50 mg, was used to sample the plants. Upper leaves were sampled twice, at 19 and 28 dpi. Two #8 sized discs were taken at each sampling. These leaf discs were analyzed for the presence of PVY coat protein antigen by ELISA. No coat protein antigen was detected in the transgenic plants. The Russet Burbank control line became highly infected resulting in 8 out of 10 plants becoming infected. In contrast, the replicase lines exhibited almost complete resistance to the virus.

TABLE 3

PROTECTION-POTATO (Russet Burbank)

| CONSTRUCT | LINE# | RNA expression | (% INFECTION) 19 DPI | 28 DPI |
|---|---|---|---|---|
| RBID control | | | 70 | 80 |
| pMON18678 | 5 | + | 0 | 0 |
| (REPLICASE) | 7 | + | 0 | 0 |
| | 10 | + | 7 | 14 |
| | 11 | + | 0 | 0 |
| | 13 | – | 0 | 0 |

Results of protection test on Russet Burbank transgenic lines expressing replicase. Plants were inoculated with 20 μg/ml PVY and assayed for virus at 19 and 28 days post inoculation (DPI). Values given represent the percentage of plants susceptible to infection. ± means either presence or absence, respectively.

All publications and patent applications mentioned in this specification are indicative of the level of skill of those skilled in the art to which this invention pertains.

From the foregoing, it will be seen that this invention is one well adapted to attain all the ends and objects hereinabove set forth together with advantages that are obvious and that are inherent to the invention. It will be understood that certain features and sub-combinations are of utility and can be employed without reference to other features and subcombinations. This is contemplated by and is within the scope of the claims. Because many possible embodiments can be made of the invention without departing from the scope thereof, it is to be understood that all matter herein set forth or shown in the accompanying drawings is to be interpreted as illustrative and not in a limiting sense.

BIBLIOGRAPHY

Abel et al. (1986) *Science* 232: 738–743.
Bevan (1984) *Nucl. Acids Res.* 12: 8711–8721.
Coruzzi et al. (1990) *EMBO J.* 3:1671.
Cuozzo et al. (1988) *BioTechnol.* 6: 549–557.
deBokx (1972) Viruses of Potatoes and Seed-Potato Production. p. 233. Centre for Agric. Publ. and Documentation, Wageningen, The Netherlands.
deBokx (1986) Potato Virus Y. in: Compendium of Potato Diseases p. 7–71. W. Hooker ed. American Phytopathology Society. Ditta et al. (1980) *Proc. Natl. Acad. Sci. USA* 77: 7347–7351.
Fling et al. (1985) *Nucl. Acids Res.* 13: 7095–7106.
Fraley et al. (1983) *Proc. Natl. Acad. Sci. USA* 80: 4803–4807.
Garcia et al., *Virology,* (1992) 188: 697–703.
Garcia-Bustos et al., *Biochimica et Biophysica Acta* 1071: 83–101 (1991).
Golemboski et al. (1990) *Proc. Natl. Acad. Sci. USA* 87: 6311–6315.
Hemenway et al. (1988) *EMBO J.* 7: 1273–1280.
Hemenway et al. (1990) *Virology* 175: 365–371.
Herrera-Estrell (1988) *Nature* 303: 209.
Hodgman (1988) *Nature* 333: 22–23.
Horsch et al. (1985) *Science* 227: 1229–1231.
Huisman et al. (1988) *J. Gen. Virol.* 69: 1789–1798.
Ishikawa et al. (1986) *Nucleic Acid Res.* 14: 8291–8305.
Ivanoff et al., *Proc. Nat'l Acad. Sci.* 83: 5392–5396 (1986)
Kaniewski et al. (1990) *Biotechnol.* 8:750–754.
Kay et al. (1987) *Science* 236: 1299–1302.
Klee et al. (1985) *BioTechnol.* 3: 637–642.
Koncz and Schell (1986) *Mol. Gen. Genet.* 204: 383–396.
Kunkel (1985) *Proc. Natl. Acad. Sci. USA* 82: 488–492.
Lawson et al. (1990) *BioTechnol.* 8: 127–134.
Mc Cormick et al. (1986) *Plant Cell Reports* 5: 81–84.
Odell et al. (1985) *Nature* 313: 810–812.
Purcifull and Edwardson (1981) in: Handbook of Plant Virus Infections and Comparative Diagnosis. E. Kurstak (ed). Elsevier/North Holland Biomedical Press.
Riechmann et al., *Journal of General Virology,* (1992) 73: 1–16.
Skryabin et al. (1988) *FEBS Lett.* 240: 3340.
Stalker et al. (1981) *Mol. Gen. Genet.* 181: 8–12.
Stark and Beachy (1989) *BioTechnol.* 7: 1257–1262.
Taschner et al. (1991) *Virology* 181: 445–450.
Todd, (1957) *Proc 3rd Conf. Potato Virus Diseases* p. 132. Lisse-Wageninger, The Netherlands.
Thomas (1980) *Proc. Natl. Acad. Sci. USA* 77: 5201–5205.
Tumer et al. (1987) *EMBO J.* 6:1181–1188.
Vance (1991) *Virology,* 182: 486–494.
van Dun et al. (1988) *Virology* 163: 572–578.
van Dun et al. (1988) *Virology* 164: 383–389.
Zuidema et al. (1980) *J. Gen. Virol.* 70: 267–276.

---

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 1569 base pairs
        (B) TYPE: nucleic acid
        (C) STRANDEDNESS: double
        (D) TOPOLOGY: linear     (ii) MOLECULE TYPE: DNA (genomic)

(xi) SEQUENCE DESCRIPTION: SEQ ID NO:1:

```
ATGGCTAAGC ATTCTGCATG GATGTTTGAA GCCTTGACGG GAAATTTGCA AGCTGTCGCA      60

ACAATGAAGA GCCAATTAGT AACCAAGCAT GTAGTTAAAG GAGAGTGTCG ACACTTCAAG     120

GAATTCCTGA CTGTGGATGC AGAGGCAGAG GCAGAGGCAT TCTTCAGGCC TTTGATGGAT     180

GCGTATGGGA AAAGCTTGCT GAACAGAGAT GCGTACATCA AGGACATAAT GAAGTATTCA     240

AAACCTATAG ATGTTGGTAT CGTGGATCGG ATGCATTCGA GGAAGCCATC AATAGGGTTA     300

TCATCTACCT GCAATGTGCA CGGCTTCAAG AAGTGTGCAT ATGTCACTGA CGAGCAAGAA     360

ATTTTCAAAG CGCTCAACAT GAAAGCTGCA GTCGGAGCCA GTTATGGGTG CAAAAAGAAA     420

GACTATTTTG AGCATTTCAC TGATGCAGAT AAGGAAGAAA TAGTCATGCA AAGCTGTCTG     480

CGATTGTATA AAGGCTTGCT CGGCATTTGG AATGGATCAT TGAAGGCAGA GCTCCAATGT     540

AAGGAAAAGA TACTTGCAAA TAAGACGAGG ACGTTCACTG CTGCACCTCT AGACACTTTG     600

CTGGGTGGTA AAGTGTGTGT TGACGACTTC AATAATCAAT TTTATTCGAA GAATATTGAG     660

TGCTGTTGGA CAGTTGGGAT GACTAAGTTT TATGGCGGTT GGGATAAACT GCTTCGGCGT     720

TTACCTGAGA ATTGGGTATA CTGTGATGCT GACGGCTCAC AGTTTGATAG TTCACTAACT     780

CCATACTTAA TCAATGCTGT TCTCACCATC AGAAGCACGT ACATGGAAGA CTGGGATGTG     840

GGGTTGCAAA TGCTGAGTAA TTTATACACT GAGATTGTTT ACACACCTAT TTCAACTCCA     900

GATGGAACAA TTGTTAAGAA GTTCAGAGGA AATAACAGTG GTCAGCCTTC TACTGTTGTG     960
```

```
GACAACTCTC TTATGGTCGT CCTTGCCATG CACTATGCTT TCATCAAAGA ATGCATTGAG    1020

TTTGAAGAGA TTGACAGCAC GTGCGTGTTC TTTGTCAATG GTGATGATTT GCTGATTGCT    1080

GTGAATCCGG ATAAAGAGAG CATTCTTGAC AGATTGTCAC AACACTTCTC AGATCTTGGT    1140

TTGAATTATG ATTTTTCGTC AAAGACAAGA AATAAGGAAG AGTTGTGGTT TATGTCTCAT    1200

AGGGGCCTAC TGATTGAGGG CATGTACGTG CCGAAACTTG AAGAGGAAGG ATTTGTGTCC    1260

ATTCTCCAAT GGGACAGAGC AGACTTGGCT GAACACAGGC TTGAGGCGAT TTGCGCAGCT    1320

ATGATAGAGT CCTGGGGTTA TTCTGAACTA ACACACCAAA TCAGGAGATT CTACTCATGG    1380

TTATTGCAAC AGCAACCTTT TGCAACAATA GCGCAGGAAG GGAAGGCTCC TTATATAGCA    1440

AGCATGGCAC TAAGGAAACT GTATATGGAT AGGGCTGTGG ATGAGGAAGA GCTAAGAGCC    1500

TTCACTGAAA TGATGGTCGC ATTAGACGAT GAGTTTGAGT TTGACTCTTA TGAAGTACAC    1560

CATCAATAG                                                            1569
```

(2) INFORMATION FOR SEQ ID NO:2:

(i) SEQUENCE CHARACTERISTICS:
        (A) LENGTH: 36 base pairs
        (B) TYPE: nucleic acid
        (C) STRANDEDNESS: single
        (D) TOPOLOGY: linear     (ii) MOLECULE TYPE: DNA (synthetic)

(xi) SEQUENCE DESCRIPTION: SEQ ID NO:2:

```
GATGTAGTGG TGGCCATGGC TAAGCATTCT GCATGG                               36
```

(2) INFORMATION FOR SEQ ID NO:3:

(i) SEQUENCE CHARACTERISTICS:
        (A) LENGTH: 41 base pairs
        (B) TYPE: nucleic acid
        (C) STRANDEDNESS: single
        (D) TOPOLOGY: linear     (ii) MOLECULE TYPE: DNA (synthetic)

(xi) SEQUENCE DESCRIPTION: SEQ ID NO:3:

```
GAAGTACACC ATCAATAGAA TGGATCCACA ATTGATGCAG G                         41
```

(2) INFORMATION FOR SEQ ID NO:4:

(i) SEQUENCE CHARACTERISTICS:
        (A) LENGTH: 597 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:4:

```
TCATCAAAAT ATTTAGCAGC ATTCCAGATT GGGTTCAATC AACAAGGTAC GAGCCATATC      60

ACTTTATTCA AATTGGTATC GCCAAAACCA AGAAGGAACT CCCATCCTCA AAGGTTTGTA     120

AGGAAGAATT CTCAGTCCAA AGCCTCAACA AGGTCAGGGT ACAGAGTCTC CAAACCATTA     180

GCCAAAAGCT ACAGGAGATC AATGAAGAAT CTTCAATCAA AGTAAACTAC TGTTCCAGCA     240

CATGCATCAT GGTCAGTAAG TTTCAGAAAA AGACATCCAC CGAAGACTTA AAGTTAGTGG     300

GCATCTTTGA AAGTAATCTT GTCAACATCG AGCAGCTGGC TTGTGGGGAC CAGACAAAAA     360

AGGAATGGTG CAGAATTGTT AGGCGCACCT ACCAAAAGCA TCTTTGCCTT TATTGCAAAG     420

ATAAAGCAGA TTCCTCTAGT ACAAGTGGGG AACAAAATAA CGTGGAAAAG AGCTGTCCTG     480
```

```
ACAGCCCACT CACTAATGCG TATGACGAAC GCAGTGACGA CCACAAAAGA ATTCCCTCTA      540

TATAAGAAGG CATTCATTCC CATTTGAAGG ATCATCAGAT ACTAACCAAT ATTTCTC        597
```

We claim:

1. A DNA molecule which comprises in the 5' to 3' direction:
  (a) a promoter region which functions in plant cells to cause the production of an RNA sequence, operably linked to
  (b) a structural gene encoding a full length replicase from a potyvirus selected from the group consisting of tobacco vein mottling virus, watermelon mosaic virus, zucchini yellow mosaic virus, bean common mosaic virus, bean yellow mosaic virus, soybean mosaic virus, peanut mottle virus, beet mosaic virus, maize dwarf mosaic virus, sorghum mosaic virus, sugarcane mosaic virus, plum pox virus, tobacco etch virus, sweet potato feathery mottle virus, yam mosaic virus, and papaya ringspot virus, operably linked to
  (c) a 3' non-translated DNA sequence which functions in plant cells to cause the termination of transcription and the addition of polyadenylated ribonucleotides to the 3' end of the transcribed mRNA sequence.

2. A DNA molecule according to claim 1 wherein said promoter region is selected from the group consisting of the FMV35S promoter region, the CaMV35S promoter region, and the enhanced CaMV35S promoter region.

3. A DNA molecule according to claim 1 wherein said promoter region is the FMV35S promoter region (SEQ ID NO. 4) as shown in FIG. 4.

4. A DNA molecule according to claim 1 wherein said 3' non-translated region is selected from the group consisting of nopaline synthase (NOS) genes, soybean 7S storage protein genes, and small subunit of the ribulose 1,5-bisphosphate carboxylase-oxygenase (ssRUBISCO) gene.

5. A DNA molecule according to claim 1 wherein said 3' non-translated region is from the pea small subunit of the ribulose 1,5-bisphosphate carboxylase-oxygenase (ssRUBISCO) E9 gene.

6. A method for providing resistance to infection by a potyvirus in a susceptible plant which comprises:
  (a) transforming plant cells with a DNA molecule encoding a full length replicase from a potyvirus which is capable of infecting said plant, the potyvirus selected from the group consisting of tobacco vein mottling virus, watermelon mosaic virus, zucchini yellow mosaic virus, bean common mosaic virus, bean yellow mosaic virus, soybean mosaic virus, peanut mottle virus, beet mosaic virus, maize dwarf mosaic virus, sorghum mosaic virus, sugarcane mosaic virus, plum pox virus, tobacco etch virus, sweet potato feathery mottle virus, yam mosaic virus, and papaya ringspot virus;
  (b) regenerating said plant cells to provide a differentiated plant; and
  (c) selecting a transformed plant which expresses the full length potyvirus replicase gene at a level sufficient to render the plant resistant to infection by said potyvirus.

7. A method according to claim 6 wherein said plant is selected from the group consisting of the plant families Solanaceae, Chenopodiaceae, Gramineae, Compositae, Leguminosae, Dioscoreaceae, Cucurbitaceae, and Caricaceae.

8. A method according to claim 6 wherein said plant is from the family Solanaceae.

9. A method according to claim 6 wherein said plant is selected from the group consisting of potato, tomato, and tobacco.

10. A stably transformed viral resistant plant which contains in its genome a DNA molecule which comprises in the 5' to 3' direction:
  (a) a promoter region which functions in plant cells to cause the production of an RNA sequence, operably linked to
  (b) a structural gene encoding a protein consisting essentially of a full length replicase from a potyvirus selected from the group consisting of tobacco vein mottling virus, watermelon mosaic virus, zucchini yellow mosaic virus, bean common mosaic virus, bean yellow mosaic virus, soybean mosaic virus, peanut mottle virus, beet mosaic virus, maize dwarf mosaic virus, sorghum mosaic virus, sugarcane mosaic virus, plum pox virus, tobacco etch virus, sweet potato feathery mottle virus, yam mosaic virus, and papaya ringspot virus, operably linked to
  (c) a 3' non-translated DNA sequence which functions in plant cells to cause the termination of transcription and the addition of polyadenylated ribonucleotides to the 3' end of the transcribed mRNA sequence.

11. A plant according to claim 10 wherein the plant is selected from the group consisting of tomato, pepper, cucurbits, wheat, corn, sorghum, peanuts, beans, and tobacco.

12. A stably transformed plant cell which contains in its genome a DNA molecule which comprises in the 5' to 3' direction:
  (a) a promoter region which functions in plant cells to cause the production of an RNA sequence, operably linked to
  (b) a structural gene encoding a full length replicase from a potyvirus selected from the group consisting of tobacco vein mottling virus, watermelon mosaic virus, zucchini yellow mosaic virus, bean common mosaic virus, bean yellow mosaic virus, soybean mosaic virus, peanut mottle virus, beet mosaic virus, maize dwarf mosaic virus, sorghum mosaic virus, sugarcane mosaic virus, plum pox virus, tobacco etch virus, sweet potato feathery mottle virus, yam mosaic virus, and papaya ringspot virus, operably linked to
  (c) a 3' non-translated DNA sequence which functions in plant cells to cause the termination of transcription and the addition of polyadenylated ribonucleotides to the 3' end of the transcribed mRNA sequence.

13. A plant cell according to claim 12 wherein the plant cell is from a plant selected from the group consisting of tomato, pepper, cucurbits, wheat, corn, sorghum, peanuts, beans, and tobacco.

* * * * *